(12) United States Patent
Levy et al.

(10) Patent No.: US 8,277,749 B2
(45) Date of Patent: Oct. 2, 2012

(54) TIME-TEMPERATURE INDICATOR BASED ON VALENCE ISOMERIZATIONS

(75) Inventors: Yoav Levy, Ramat Hasharon (IL); Dietrich Haarer, Bayreuth (DE)

(73) Assignee: Freshpoint Holdings S.A., Lachaux-de-Fonds (CH)

( * ) Notice: Subject to any disclaimer, the term of this patent is extended or adjusted under 35 U.S.C. 154(b) by 1451 days.

(21) Appl. No.: 10/587,586

(22) PCT Filed: Jan. 24, 2005

(86) PCT No.: PCT/EP2005/050291
§ 371 (c)(1),
(2), (4) Date: Jul. 28, 2006

(87) PCT Pub. No.: WO2005/075978
PCT Pub. Date: Aug. 18, 2005

(65) Prior Publication Data
US 2007/0172951 A1    Jul. 26, 2007

Related U.S. Application Data

(60) Provisional application No. 60/540,558, filed on Feb. 2, 2004, provisional application No. 60/564,232, filed on Apr. 22, 2004.

(51) Int. Cl.
*G01N 33/02* (2006.01)
*G01N 31/22* (2006.01)
(52) U.S. Cl. ........... 422/400; 422/430; 436/1; 436/2; 436/164; 426/87; 426/88; 426/232
(58) Field of Classification Search ............. 422/400, 422/430; 436/1, 2, 164; 426/87, 88, 232
See application file for complete search history.

(56) References Cited

U.S. PATENT DOCUMENTS

| | | | |
|---|---|---|---|
| 3,038,812 A | 6/1962 | Berman et al. | |
| 3,397,059 A | 8/1968 | Dorion et al. | 96/87 |
| 5,376,511 A | 12/1994 | Tatezono et al. | 430/495 |
| 5,710,420 A | 1/1998 | Martin et al. | 235/487 |
| 5,782,969 A | 7/1998 | Takagi | 106/498 |

(Continued)

FOREIGN PATENT DOCUMENTS
WO    WO01/86289    11/2001

OTHER PUBLICATIONS

Spectrophotomtric study of the isomerization of various thermochromic spirans Bloch-Chaude, Odile; Cahiers de Physique (1954), No. 50; No. 51;No. 52, 17-53;6-42;3-48;CODEN: CAPHAI; ISSN: 0366-5291.*

(Continued)

*Primary Examiner* — Lyle Alexander
(74) *Attorney, Agent, or Firm* — Wenderoth, Lind & Ponack, L.L.P.

(57) ABSTRACT

The present invention relates to a time temperature indicator comprising at least one indicator compound in a first isomeric form, which is converted into a second isomeric form of said indicator compound in a valence isomerization reaction without migration of an atom or chemical group attached to said indicator compound in a time and temperature dependent manner, wherein the formation of the second isomeric form is detectable by monitoring a physical characteristic of the indicator. The present invention also relates to a method of manufacturing such a time-temperature indicator comprising the steps of (a) embedding in or atop a matrix said indicator compound; and (b) inducing the formation of a metastable state of said embedded indicator compound.

23 Claims, 6 Drawing Sheets

U.S. PATENT DOCUMENTS

| | | | |
|---|---|---|---|
| 6,084,702 A * | 7/2000 | Byker et al. | 359/288 |
| 2003/0139903 A1 * | 7/2003 | Zweig et al. | 702/182 |
| 2004/0178394 A1 | 9/2004 | Tanaka et al. | 252/586 |

OTHER PUBLICATIONS

Dynamic behavior of sol-gel gel-glass based thermochromic material applied toward development of practical optical temperature Matias, Ignacio R et al., Optical Engineering (Bellingham, Washington) (1998), 37(9), ISSN: 0091-3286 PB SPIE—The International Society for Optical Engineering.*

D. A. Topchiyev, Polymer Science USSR, vol. 32, No. 12, pp. 2361-2383, XP 000244248, (1990).

* cited by examiner

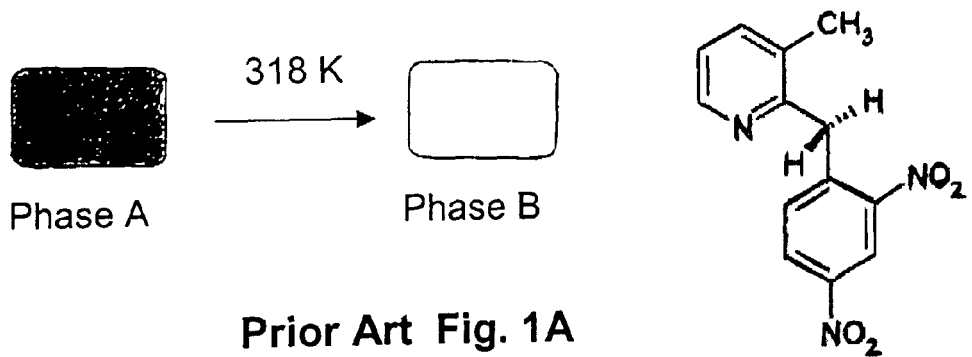
Prior Art Fig. 1A
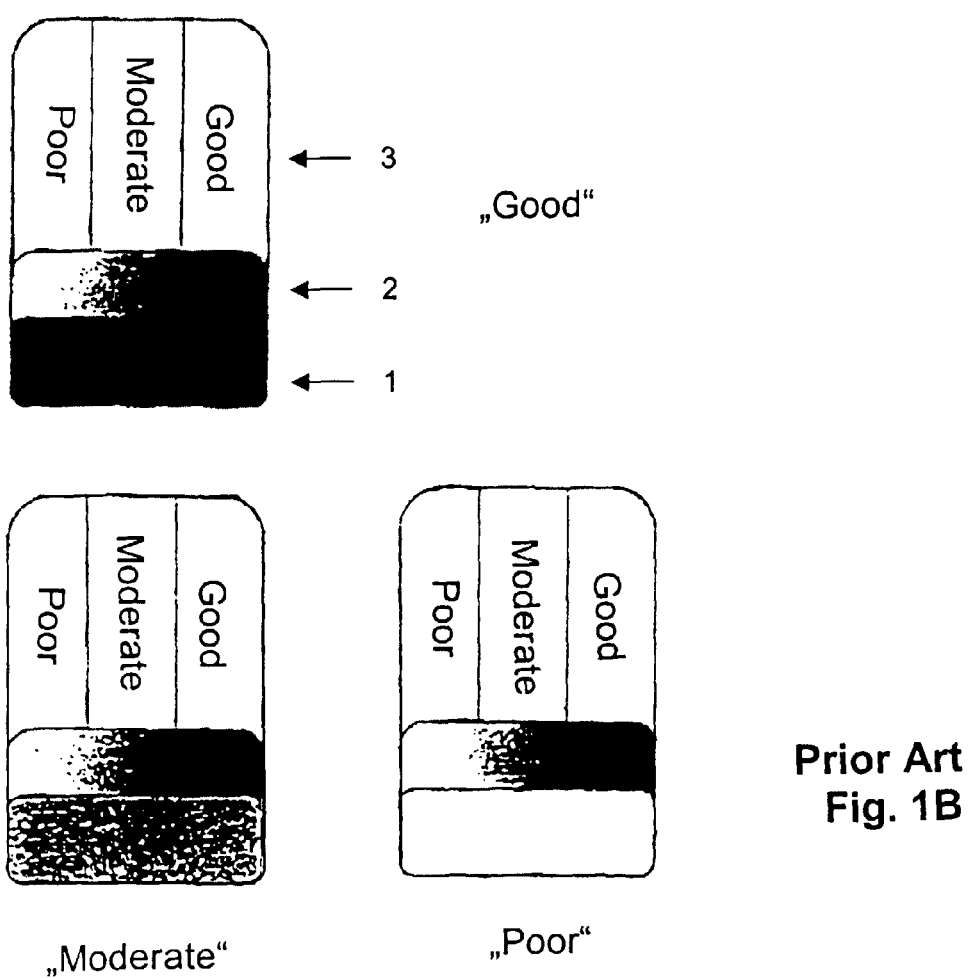
"Good"
"Moderate" "Poor"
Prior Art Fig. 1B

TIME-TEMPERATURE INDICATOR BASED ON VALENCE ISOMERIZATIONS

This application is a U.S. national stage of International Applicaton No. PCT/EP05/050291, filed Jan. 24, 2005, which claims the benefit of U.S. Provisional Application No. 60/540,558, filed Feb. 2, 2004, and claims the benefit of U.S. Provisional Application No. 60/564,232, filed Apr. 22, 2004.

The present invention relates to a time temperature indicator comprising at least one indicator compound in a first isomeric form, which is converted into a second isomeric form of said indicator compound in a valence isomerization reaction without migration of an atom or chemical group attached to said indicator compound in a time and temperature dependent manner, wherein the formation of the second isomeric form is detectable by monitoring a physical characteristic of the indicator. The present invention also relates to a method of manufacturing such a time-temperature indicator comprising the steps of (a) embedding in or atop a matrix said indicator compound; and (b) inducing the formation of a metastable state of said embedded indicator compound.

Time-temperature indicators, TTIs, are substrates for packaging of or attachment to perishable goods that are capable of reporting the partial or full time temperature history of any good to which it is thermally coupled.

Temperature abuse is one of the most frequently observed causes for predated goods spoilage. It is therefore important and desired to monitor the time-temperature history of such perishable goods, preferably, using inexpensive and consumer friendly means. Time temperature indicators are substances that are capable of visually reporting on the summary of the time temperature history of the substance, and consequently, of the perishable good it is associated with. Designed for the end user, time temperature indicators are usually designed to report a clear and visual Yes/No signal.

U.S. Pat. No. 3,999,946 proposes providing the perishable products with an indicator giving the time/temperature history. According to the length of storage and the storage temperature of the product, the originally colourless acetylene-based indicator exhibits a characteristic, irreversible colour change from which the quality of the stored perishable product can be inferred.

U.S. Pat. No. 5,053,339 (WO 92/09870) describes a time-temperature indicator (TTI) which consists of a layer comprising the indicator, a barrier layer that is impermeable to the indicator and permeable to the activator, and a layer comprising the activator. In dependence upon the temperature, the activator diffuses through the barrier layer into the indicator layer, where it provides a change in colour.

WO 99/39197 describes the use of photochromic dyes, based on a transfer reaction and embedded in the crystalline state, as active materials for TTIs. TTIs based on these materials are highly accurate and reproducible and can be charged using stimulating light. Some basic limitations of most photochromic materials arise from the fact that the colored photoproduct is sufficiently photoactive to introduce undesired light effects to the time temperature profile. Often, photobleaching of the colored species is achieved even by modest ambient light. According to WO 99/39197, this problem can be overcome by placing a special filter atop the active substance, thus filtering most of the UV and visible spectrum. In the prior art document WO 99/39197, the photochromic indicators are based on a transfer reaction that is understood as being a reaction, which includes a change in the atomic connectivities and the rearrangement of at least one atom being involved, for example the transfer of a hydrogen atom (or a proton or hydride).

Starting from the prior art, there is a confusing variety of possible indicators to be used, without any pointers being given to possible further improvements. WO 99/39197 merely teaches that indicators with photochromic properties being capable to undergo transfer reactions can be used. Among other factors, light and fatigue resistance upon repeated cycles of coloring and decoloring of the time-temperature indicator systems disclosed in WO 99/39197 are still unable to meet satisfactorily all of the ever growing demands.

Thus, there is a need for a commercial TTI that is inexpensive with regard to the manufacturing costs and that provides for clear visual information, which should enable a reliable electronic readout. Also, the information drawn from the TTI must be highly accurate and reproducible, particularly said information must be fully proportional to the time-temperature history. Finally, such a TTI should be printable on a commercially used substrate, for example packaging material for food items and further, the TTI should be stable enough to allow storage at room temperature before its activation. The problem underlying the present invention is therefore to provide a time-temperature indicator system that overcomes the shortcomings of the existing prior art time-temperature indicators and which has the afore-mentioned beneficial features of a commercially interesting TTI.

Surprisingly, the present invention solves the underlying problem and avoids the disadvantages in the prior art in that it provides a novel time-temperature indicator (TTI) system that is based on a pure valence isomerization reaction of the indicator compound. This valence isomerization of the indicator compound being the active material of such a TTI comprises the conversion of a first isomeric form of this compound into a second isomeric form without migration of an atom or group attached to the indicator compound. Preferably, the active material of the TTI is capable to undergo valence isomerization in both directions, i.e. capable to be converted into the second isomeric form from the first isomeric form and vice versa. These specific indicator compounds are termed hereinafter as reversible indicator compounds.

A first embodiment of the present invention therefore relates to a time temperature indicator for indicating a temperature change over time, comprising at least one indicator compound in a first isomeric form, which is converted into a second isomeric form of said indicator compound in a valence isomerization reaction without migration of an atom or chemical group attached to said indicator compound in a time and temperature dependent manner, wherein the formation of the second isomeric form is detectable by monitoring a physical characteristic of the indicator. The physical characteristic can be any inherent property of the first isomeric or the second isomeric form of the indicator provided it produces a detectable signal that allows distinguishing the first isomeric form from the second isomeric form of said indicator compound and corresponds to the concentration of the first isomeric form or the second isomeric form such that the detectable signal shed light on the reaction progress. Preferably, the indicator compound is in a crystallite form.

It is also preferred when the inventive time-temperature indicator is based on a valence isomerization reaction, which comprises an intramolecular ring closure or ring opening step as part of the conversion of the first isomeric form of the indicator compound into the second isomeric form.

It is also preferred that the formation of the second isomeric form of the indicator compound is associated with a change of color and the valence isomerization progress can be detected by monitoring the color of the first or the second isomeric indicator form. For example, the first isomeric form is colored and the second isomeric form is a pale or colorless reaction product. Alternatively, the first isomeric form is colored and the second isomeric form is pale or colorless. However, the physical characteristic of both isomeric forms, which is linked to its concentration is not limited to a color of the visible spectrum but also includes absorption and/or emission at a wavelength within the IR or UV range.

The term valence isomerization is to be understood as being a reaction wherein sigma and/or pi bonds are cleaved and/or newly formed, wherein distances between atoms and bond angle values are changed, wherein ring opening, ring diminishment and ring enlargement steps or other ring reactions occur. However, these reactions do not include the migration of an atom or a chemical group attached to the compound that undergoes such an isomerization process. Valence isomerizations are induced by thermal or photochemical energy and generally reversible processes. Typical valence isomerizations include electrocyclic reactions comprising the conversion of single and double bonds or sigmatropic reactions characterized in that the number of single and double bonds is kept unchanged. Valence isomerizations follow the Woodward-Hoffmann rules and can be classified as synchronously running multiple centers reactions and are also termed as pericyclic reactions.

Preferably, the inventive TTI relies on a reversible photochromic indicator compound. By virtue of its photochromic properties, the indicator compound can undergo photo-induced coloration by irradiation with photons of a specific energy range (conversion of the second isomeric form into the first isomeric form), the coloration being followed by a time- and temperature-dependent decoloration (conversion of the first isomeric form into the second isomeric form). The coloration of the indicator compound can take place at a defined timepoint, preferably, for example, immediately after printing onto a substrate, which is especially the packaging of a perishable material. It is preferred when the photochromic indicator compound being the active material of the TTI is in a crystallite form.

For example, the initially colorless indicator compound is irradiated with UV light or near-UV light, whereupon a valence isomerization within the indicator compound (conversion of the second isomeric form into the first isomeric form) and an associated indicator compound coloration takes place. Such a photo-induced valence isomerization then proceeds as a function of time and temperature in the other direction again, so that the indicator is successively decolorised. Compared to previously described TTI systems, for example those disclosed in WO 99/39197 which are based on transfer reactions, the activation energy necessary to convert the second isomeric form of the indicator compound into the first isomeric form is generally much higher. For example, the migration of a single proton in a proton transfer reaction is less energy consuming than the structural rearrangment of the carbon backbone of a complex organic compound due to valence isomerization. Especially, valence isomerization reactions, which include a ring opening and/or a ring closure step are associated with major conformational changes that are reflected by increased activation energies. Based on the higher activation energies, it is now possible to design TTIs that are capable to cover a larger range of time temperature indication than it is possible with the existing TTI systems. All indicator compounds mentioned hereinafter are photochromic when being present in their crystalline form. Further, the photochromic indicator compounds described hereinafter are characterized by a large number of potential derivatization sites. Since even the introduction of small substituents will generally have a strong effect on the packing of the molecules within the crystal, a broad range of different activation energies will characterize the resulting TTI derivatives. This provides for the option to create a whole TTI family starting from a single parent indicator compound by simply varying the substitution pattern of said indicator compound.

The time-temperature clock can accordingly be started at a defined desired timepoint and does not begin to run irreversibly at the time of the indicator synthesis. Decoloration is preferred for consideration according to the invention, but the use of an indicator in which the coloration process forms the basis of the time-temperature clock is also conceivable.

After printing and activation, the time-temperature integrator is, if necessary, provided with a protector, which prevents the renewed photo-induced coloration of the reversible indicator. Such a protector may be a protective coating (overprint varnish) or a laminate that comprises a filter, which, by filtering out certain wavelength ranges, is intended to prevent undesirable renewed coloration of the indicator after the time-temperature clock has started.

In addition, for the purpose of tamper-proofing, it is possible for a further, irreversible indicator to be arranged e.g. alongside or over the reversible indicator. The further indicator indicates by means of an irreversible color change that the reversible indicator has undergone renewed coloration after production or packaging of the perishable goods.

It is also possible to use indicators having more than one characteristic time domain. Such indicators can have, for example, a phase transition, with the different phases exhibiting different decoloration behaviours. The simultaneous use of two or more indicators having different time domains is likewise possible. Also, it is possible to include other indicators, for example those indicating storage of the perishable product at a temperature exceeding a predetermined limit.

In a preferred embodiment, the present invention relates to a time-temperature indicator comprising an active material that includes at least one compound selected from diarylethenes, preferably diarylethenes of Formula I (see below) and spiroaromatics, preferably spiroaromatics of Formula II (see below). Preferably, said active material is in a crystallite form.

Diarylethenes and spiroaromatic compounds are reversible and bistable photochromic materials that exhibit a change in color in response to time and/or temperature changes, as well as light changes.

Diarylethenes exist in an open and a cyclic isomeric form that can be converted into each other by valence isomerization. Diarylethenes are preferred wherein the open form is transparent, while the cyclic form is colored and wherein the open form is the thermodynamically stable species, while the dosed form is either a stable state or a metastable one. One specific example of the reversible process of ring-closure/ring-opening of diarylethene, namely, of styrene is shown below.

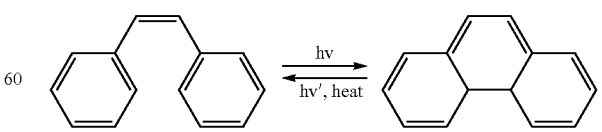

The most striking feature of these compounds is their resistance to fatigue. The coloration-discoloration cycle could be repeated more than $10^4$ times maintaining the photochromic performance.

In spiroaromatic compounds according to the present invention, there are also two isomeric forms, an open and a cyclic isomeric form that can be converted into each other by valence isomerization. Spiroaromatic derivatives are preferred wherein the dosed form is the thermodynamically stable state:

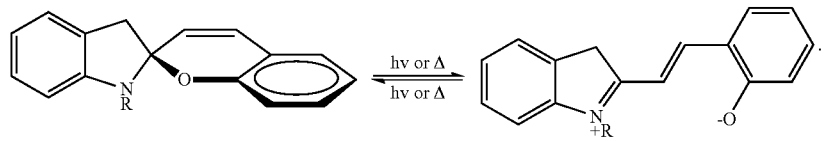

In cases where the activation energy is appropriate, the ring opening of the closed form of diarylethenes and the ring closure of spiroaromatic materials can be utilized in the monitoring of the time temperature history of the material, relaying on the color change associated with these processes.

Of all diarylethene and spiroaromatic derivatives, materials that exhibit the following characteristics are especially suitable for TTI applications:

(1) the system has at least one thermal process leading from one metastable state to one stable state, where the two states are characterized beta distinctly different color and/or any other measurable physical parameter such as luminescence, refraction index, conductivity and the like.

(2) the stable state may be converted to the metastable state using one or any combination of stimuli, among others the following processes: a) photonic induction, b) thermal induction, c) pressure induction, d) electrical induction, or e) chemical induction; and (3) other than temperature, the metastable state is substantially not affected by anyone or any combination of stimuli such as a) photo induction, b) piezo induction, c) electro induction, d) chemo induction.

The active material of the present invention may be in the form of a crystal or a polycrystalline powder, in which the forward and reverse reactions take place or alternatively may be in a form of any other solid phase such as a glass, a polymer solution or attached to a polymer, or in the form of a liquid or a solution.

In accordance with a preferred aspect of the present invention, the active material suitable for use in time temperature indicators comprise one or more compounds having the diarylethene backbone, which fulfill the requirements disclosed hereinabove and has general Formula (I):

wherein
R1 and R2 each independently represents C6-C14 aryl, C4-C1-2 heteroaryl, conjugated heterocyclic; wherein said heteroaryl and conjugated heterocyclic may contain one to three heteroatoms selected from N, O, or S; and wherein said aryl, heteroaryl, or conjugated heterocyclic may be substituted by one or more halogen, hydroxyl, thiol, amino, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, cyano, nitro, sulfo, —CH═CH—CN, azido, or amido;

R1' and R2' each independently represents H, cyano, nitro, sulfo, hydroxyl, thiol, —CH═CH—CN, or amido; or substituted or unsubstituted C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocylic, C3-C8 membered ring non-aromatic heterocyclic; or R1' and R2' together with the carbon atoms to which they are attached form a C5-C8 carbocyclic ring or a C4-C7 heterocyclic ring containing one to three endocyclic or exocyclic heteroatoms selected from N, O, or S; said N heteroatom may be further substituted by H, or by one or two substituted or unsubstituted groups selected from C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl, or —CH═CH—CN; when said N heteroatom is tetrasubstituted it is positively charged and is associated with an anion selected from the group consisting of organic or inorganic anions, and wherein said C5-C8 carbocycle may be substituted by one or more halogen, preferably by one or more fluoro atoms;

R1, R1', R2 and R2' may each represent a charged group or a group substituted by another group having a charge; said charge may be localized or delocalized and may be positive or negative, resulting from charged groups such as ammonium, phosphonium, phenolate, carboxylate, sulphonate, thiolate, selenate and the like;

and wherein said R1 and R2 may be in a cis or trans conformation.

In one embodiment, the compounds of Formula (I) are zwitterions in which one of the groups R1, R1', R2, or R2' may be positively charged and one other group may be negatively charged.

In one specific embodiment, the compounds of Formula (I) are those wherein R1 and R2 are each independently a substituted heteroaryl containing one to three heteroatoms selected from N, O, or S; wherein said heteroaryl is substituted by one or more halogen, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, cyano, nitro, sulfo, —CH═CH—CN, azido, amido or amino; R1' and R2' each independently represents H, C1-C12 alkyl, C2-C12 alkenyl, cyano, nitro, or —CH═CH—CN, or R1' and R2' together with the carbon atoms to which they are attached form a C5-C8 carbocyclic ring or a C4-C7 heterocyclic ring containing one to three endocyclic or exocyclic heteroatoms selected from N, or O; said N heteroatom is further substituted by H, or by a substituted or unsubstituted C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, or —CH═CH—CN; and wherein said C5-C8 carbocycle is substituted by one or more halogen, preferably by one or more fluoro atoms.

In another specific embodiment, R1 and R2 are identical and are selected from substituted or unsubstituted indoles, pyrroles, thiophenes, benzthiophenes or furans. In this embodiment R1' and R2' are also identical and are selected from cyano, C1-C6 alkyl, or C6-C14 aryl.

In yet another embodiment, R1 and R2 are selected from substituted or unsubstituted thiophenes, benzthiophenes, indoles or pyrroles; and R1' and R2' together with the carbon atoms to which they are attached form a cyclopentyl, cyclohexyl, or an anhydride ring; said cyclopentyl or cyclohexyl being further substituted by one or more halogen, C1-C6 alkyl, C6-C14 aryl, hydroxyl, amino, nitro, or cyano groups. Preferably, the cyclopentyl or cyclohexyl are substituted by halogens. Most preferably they are perfluorated.

Suitable diarylethenes of Formula I include both symmetric and asymmetric diarylethene compounds.

Examples of symmetric diarylethenes which are suitable for use with the TTIs of the present invention, and which are encompassed in the general Formula (I) are:

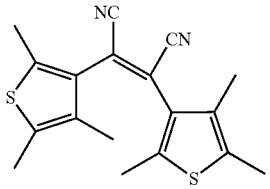

1,2-dicyano-1,2-bis(2,4,5-trimethylthiophene-3-yl) ethane (1)

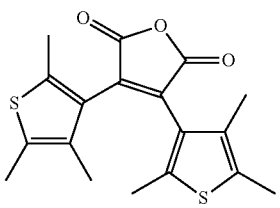

2,3-bis(2,4,5-trimethylthiophene-3-yl)maleic anhydride (2)

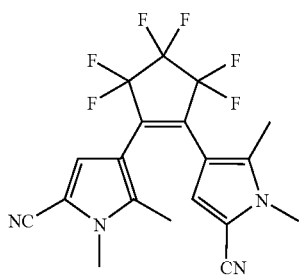

1,2-bis(2-cyano-1,5-dimethyl-4-pyrrolyl)perfluorocyclopentene (3)

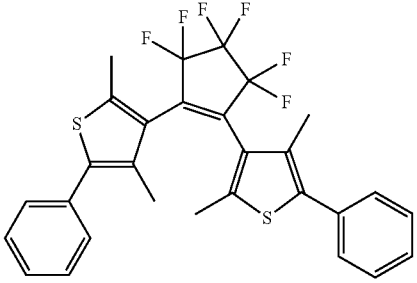

1,2-bis(2,4-dimethyl-5-phenylthiophene-3-yl)perfluorocyclopentene (4)

Examples of asymmetric diarylethenes, which are suitable for TTIs and are encompassed with in general Formula (I) are:

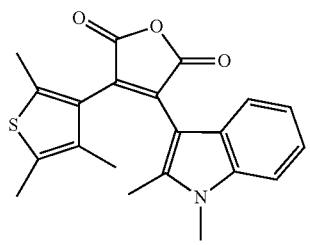

2-(1,2-dimethyl-3-indolyl)-3-(2,4,5-trimethyl-3-thienyl) maleic anhydride (5)

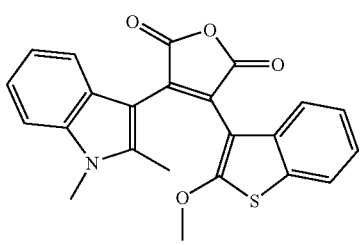

2-(methoxybenzo[b]thiophene-3-yl)-3-(1,2-dimethyl-3-indolyl) maleic anhydride (6)

In a specific embodiment of the invention, the compounds of Formula (I) are symmetric diarylethenes such as 1,2-dicyano-1,2-bis(2,4,5-trimethylthiophene-3-yl)ethane (1); 2,3-bis(2,4,5-trimethylthiophene-3-yl)maleic anhydride (2); 1,2-bis(2-cyano-1,5-dimethyl-4-pyrrolyl)perfluorocyclopentene (3); and 1,2-bis(2,4-dimethyl-5-phenylthiophene-3-yl)perfluorocyclopentene (4).

In another specific embodiment, the compounds of Formula (I) are asymmetric diarylethenes such as 2-(1,2-dimethyl-3-indolyl)-3-(2,4,5-trimethyl-3-thienyl) maleic anhydride (5); 2-(methoxybenzo[b]thiophene-3-yl)-3-(1,2-dimethyl-3-indolyl) maleic anhydride (6).

As already noted above, spiroaromatics are also suitable as indicator compounds in TTI systems according to the present invention. Spiroaromatics consist structurally of two carbocycles connected through a single carbon atom from which four extending bonds are bonding other carbon or heteroatoms. Of the four bonds, extending from the spirocarbon center, at least one is to a heteroatom allowing bond cleavage and ring opening under controllable conditions.

Spiropyrans are one class of spiroaromatics and are especially preferred. Spiropyrans consist of a pyran ring linked via a common spirocarbon center to another heterocyclic ring. Irradiation of the colorless spiropyran with UV light causes heterolytic cleavage of the C—O bond forming the ring-opened colored species, often called the "merocyanine" form which can take on a cis-(1,2) or trans-(1,3) or the ortho-quinoidal form. The pyran ring is usually a substituted benzo or naphthopyran but the heterocylic component situated across the spirocarbon center can be chosen from a long list of ring systems such as, and not limited to, indole, benzthiazole, benzoxazole, benzselenazole, quinoline, acridine, phenanthridine, benzopyran, naphthopyran, xanthane, pyrrolidine and thiazolidine.

Similarly to the arylethenes, the active material used in the present invention may be any one of spiroaromatic materials of the general Formula II:

(II)

wherein
ring A represents a C5-C8 carbocycle, C4-C7 heterocycle containing at least one heteroatom selected from N, O, or S; said N heteroatom may be further substituted by one or two groups selected from C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl, or —CH=CH—CN; when said N heteroatom is tetrasubstituted it is positively charged and is associated with an anion selected from the group consisting of organic or inorganic anions;
said C5-C8 carbocycle or C4-C7 heterocycle may be substituted by one or more of the groups selected from halogen, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, cyano, nitro, sulfo, hydroxyl, thiol, —CH=CH—CN, azido, amido or amino;
ring B represents a substituted or unsubstituted heterocycle containing at least one heteroatom X, said X being selected from N, O, and S; wherein said N atom may be further substituted by one or two groups selected from C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl, or —CH=CH—CN; when said N heteroatom is tetrasubstituted it is positively charged and is associated with an anion selected from the group consisting of organic or inorganic anions;
and wherein said ring B may contain one or more endocyclic double bonds and is optionally substituted by one or more halogen, preferably by one or more fluoro atoms;
said rings A and B may be fused to one or more substituted or unsubstituted carbocycle, C4-C14 heterocycle, C6-C14 aryl or C4-C14 heteroaryl ring system;
and wherein the compounds of Formula II may be neutral, charged, multiply charged, positively charged having an external anion, negatively charged having an external cation or zwitterionic.

Preferably, the spiroaromatic compounds of Formula (II) are those in which rings A and B each represents a C4-C7 heterocycle containing at least one heteroatom selected from N, O, or S, and wherein said N heteroatom may be further substituted by C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic or —CH=CH—CN;
said C4-C7 heterocycle is substituted by one or more group selected from halogen, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, cyano, nitro, sulfo, hydroxyl, —CH=CH—CN, azido, amido or amino;
said rings A and B may contain one or more endocyclic double bond and may also be fused to one or more substituted or unsubstituted carbocycle, C4-C14 heterocycle, C6-C14 aryl or C4-C14 heteroaryl ring system.

In a more preferred embodiment the spiroaromatic compounds of Formula (II) are spiropyran derivatives, preferably derivatives of 1',3',3'-trimethyl-6-nitro-spiro(2H-1-benzopyran-2,2'-2H-indole) as in Formula (III):

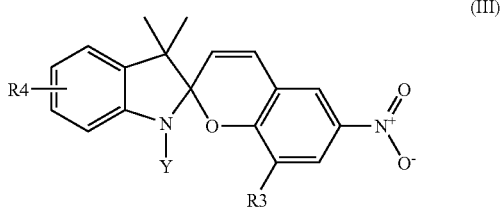

(III)

wherein
R3 is selected from the group consisting of H, halogen, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, or azido; wherein said alkyl, alkenyl, alkynyl, aryl, heteroaryl, and non-aromatic carbocycle may be substituted by one or more group selected from halogen, hydroxyl, thiol, amino, alkoxy, nitro, azido, or sulfo;
R4 is selected from the group consisting of H, halogen, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl or —CH=CH—CN; and
Y is selected from the group consisting of C1-C25 alkyl, preferably methyl, n-propyl and n-octadecyl, and C7-C15 aralkyl, wherein said alkyl and aralkyl may be substituted by one or more group selected from halogen, preferably fluorine.

In yet another preferred embodiment the spiroaromatic compounds of Formula (II) are derivatives of 1',3',3'-trimethyl-6-nitro-spiro(2H-1-benzopyran-2,2'-2H-indole) as in Formula (IV):

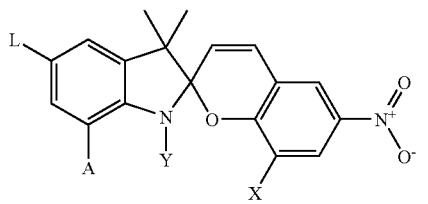

(IV)

wherein

A and L are independently of each other selected from the group consisting of H, halogen, C2-C12 alkenyl, C2-C12 alkynyl and

wherein R is C1-C6 alkyl, C1-C6 alkoxy, C6-C14 aryl and C7-C15 aralkyl; wherein said alkenyl, alkynyl and

may be substituted by one or more group selected from halogen, hydroxyl, thiol, amino, alkoxy, nitro, azido, sulfo, aryl and heteroaryl;

Y is selected from the group consisting of C1-C25 alkyl, preferably methyl, n-propyl and n-octadecyl, and C7-C15 aralkyl, wherein said alkyl and aralkyl may be substituted by one or more group selected from halogen, preferably fluorine; and X is C1-C6 alkoxy or L.

In a more preferred embodiment, the spiroaromatic compounds of Formula (II) are derivatives of 1',3',3'-trimethyl-6-nitro-spiro(2H-1-benzopyran-2,2'-2H-indole) as in Formula (IV) wherein L is H; halogen, preferably Cl, Br or I; $CH_3—(CH=CH)_n—CH=CH_2$, wherein n is an integer of from 1 to 10; or $—C≡C$-aryl, preferably $—C≡C$-phenyl;

Y is C1-C25 alkyl or

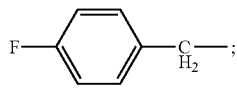

X is hydrogen, methoxy or halogen; and A is hydrogen.

It is preferred when L is I, Br or Cl; more preferred when L is I or Br; and most preferred when L is I.

It is also preferred when Y is

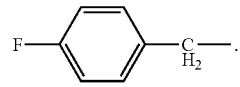

Specific examples of preferred spiroaromatic compounds for the use in the TTI according to the present invention include:

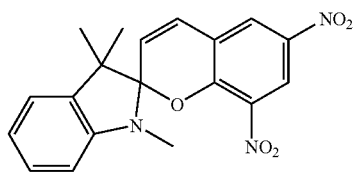

1',3',3'-trimethyl-6-nitro-spiro(2H-1-benzopyran-2,2'-2H-indole) (7)

1',3',3'-trimethyl-6,8-dinitro-spiro(2H-1-benzopyran-2,2'-2H-indole) (8)

6-(4-nitrophenylazo)-1',3',3'-trimethyl-spiro(2H-1-benzopyran-2,2'-2H-indole) (9)

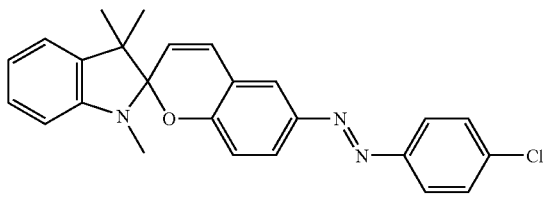

6-(4-chlorophenylazo)1',3',3'-trimethyl-spiro(2H-1-benzopyran-2,2'-2H-indole) (10)

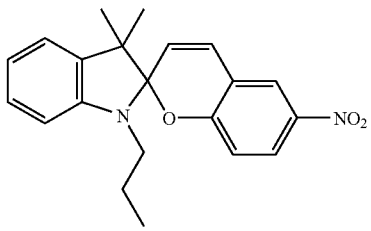

1'-propyl-3',3'-dimethyl-6-nitro-spiro(2H-1-benzopyran-2,2'-2H-indole) (11)

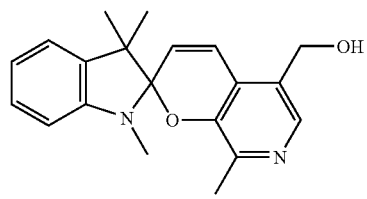

1',3',3',8-tetramethyl-5-hydroxymethyl-spiro(2H-pyrano[2,3-c]pyridine-2,2'-2H-indole) (12)

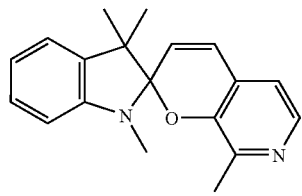

1',3',3',8-tetramethyl-spiro(2H-pyrano[2,3-]pyridine-2,2'-2H-indole). (13)

Further specific examples of preferred spiroaromatic compounds for the use in the TTI according to the present invention also include compounds (19) to (36):

(IV)

| Compound | L | Y | X |
|---|---|---|---|
| 19 | H | methyl | H |
| 20 | H | n-propyl | H |

-continued (IV)

| Compound | L | Y | X |
|---|---|---|---|
| 21 | H | n-octadecyl | H |
| 22 | H | F-C6H4-CH2- | H |
| 23 | Cl | methyl | H |
| 24 | Cl | n-propyl | H |
| 25 | Cl | n-octadecyl | H |
| 26 | Cl | F-C6H4-CH2- | H |
| 27 | Br | methyl | H |
| 28 | Br | n-propyl | H |
| 29 | Br | n-octadecyl | H |
| 30 | Br | F-C6H4-CH2- | H |
| 31 | I | methyl | H |
| 32 | I | n-propyl | H |
| 33 | I | n-octadecyl | H |
| 34 | I | F-C6H4-CH2- | H |
| 35 | H | F-C6H4-CH2- | methoxy |

The spiroaromatic compounds (22), (32) and (34) are most preferred for the use in the TTI according to the present invention.

Time-temperature indicators are especially preferred, wherein the spiroaromatic compounds of Formula (II) are selected from: 1',3',3',8-tetramethyl-5-hydroxymethyl-spiro(2H-pyrano[2,3-c]pyridine-2,2'-2H-indole) and 1',3',3',8-tetramethyl-spiro(2H-pyrano[2,3-c]pyridine-2,2'-2H-indole).

In another preferred embodiment of the inventive time-temperature indicator, the compounds of Formula (II) include at least one of the following: 1',3',3'-trimethyl-6-nitro-spiro(2H-1-benzopyran-2,2'-2H-indole); 1',3',3'-trimethyl-6,8-dinitro-spiro(2H-1-benzopyran-2,2'-2H-indole); 6-(4-nitrophenylazo)-1',3',3'-trimethyl-spiro(2H-1-benzopyran-2,2'-2H-indole); 1'-propyl-3',3'-trimethyl-6-nitro-spiro(2H-1-benzopyran-2,2'-2H-indole); and 6-(4-chlorophenylazo)-1',3',3'-trimethyl-spiro(2H-1-benzopyran-2,2'-2H-indole).

In yet another embodiment of the present invention, the compounds of Formula (II) are spiropyrans derivatives such as 1',3',3'-trimethyl-6-nitro-spiro(2H-1-benzopyran-2,2'-2H-indole); 1',3',3'-trimethyl-6,8-dinitro-spiro(2H-1-benzopyran-2,2'-2H-indole); 6-(4-nitrophenylazo)-1',3',3'-trimethyl-spiro(2H-1-benzopyran-2,2'-2H-indole); and 6-(4-chlorophenylazo)-1',3',3'-trimethyl-spiro(2H-1-benzopyran-2,2'-2H-indole).

In another specific embodiment, the spiroaromatic compounds used in the TTIs of the present invention are charged spiropyrans. The charged spiropyrans can be positively charged, negatively charged, zwitterionic or multiply charged. Preferably, these compounds are positively charged and are associated with a negatively charged counterion being an organic or inorganic counterion such as, but not limiting to, iodide, chloride, fluoride, bromide, carbonate, $PF_6^-$, $BF_4^-$, (phenyl)$_4$B$^-$, benzoate hydroxide and the like.

Specific examples of positively charged spiropyran compounds for the use in the TTI according to the present invention include:

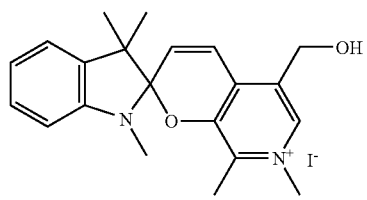

1',3',3',7,8-pentamethyl-5-hydroxymethyl-spiro(2H-pyrano [2,3-c]pyridinium-2,2'-2H-indole) iodide (14)

1',3',3', 7,8-pentamethyl-5-hydroxymethyl-spiro(2H-pyrano [2,3-c]pyridinium-2,2'-2H-indole) chloride (14a)

1',3',3', 7,8-pentamethyl-5-hydroxymethyl-spiro(2H-pyrano [2,3-]pyridinium-2,2'-2H-indole) hydroxide (14b)

1',3',3',7,8-pentamethyl-5-hydroxymethyl-spiro(2H-pyrano [2,3-c]pyridinium-2,2'-2H-indole) benzoate (14c)

1',3',3',7,8-pentamethyl-5-hydroxymethyl-spiro(2H-pyrano [2,3-c]pyridinium-2,2'-2H-indole) hexafluorophosphate (14d)

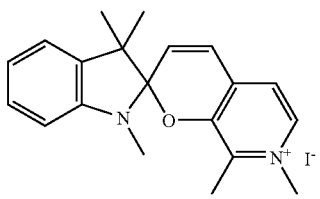

1',3',3',7,8-pentamethyl-spiro(2H-pyrano[2,3-c]pyridinium-2,2'-2H-indole)iodide (15)

1',3',3',7,8-pentamethyl-spiro(2H-pyrano[2,3-c]pyridinium-2,2'-2H-indole) chloride (15a)

1',3',3,7,8-pentamethyl-spiro(2H-pyrano[2,3-c]pyridinium-2,2'-2H-indole) benzoate (15b)

1',3',3',7,8-pentamethyl-spiro(2H-pyrano[2,3-c]pyridinium-2,2'-2H-indole)hexafluorophoaphate (15c)

1',3',3',7,8-pentamethyl-spiro(2H-pyrano[2,3-c]pyridinium-2,2'-2H-indole) hydroxide (15d).

In yet another embodiment, the compounds of Formula (II) are charged.

In another specific embodiment, the spiroaromatic compounds are spirooxazine (16) or its derivatives, spironaph thoxazine (17) or its derivatives, and spiroindolinopyridobenzoxazine (18) or its derivatives:

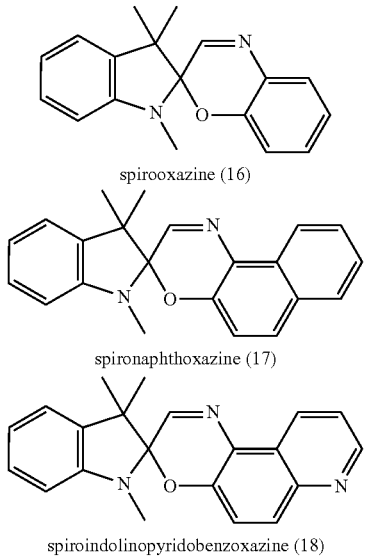

spirooxazine (16)

spironaphthoxazine (17)

spiroindolinopyridobenzoxazine (18)

Preferred derivatives of those spiroaromatic compounds include the spirooxazine derivatives (16a), spironaphthoxazine derivatives (17a) and spiroindolinopyridobenzoxazine derivatives (18a)

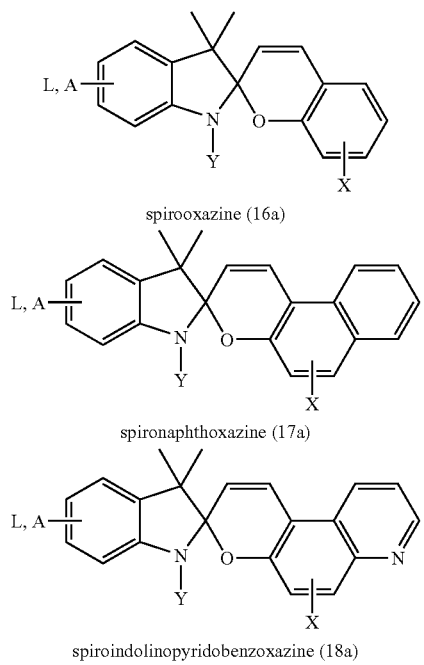

spirooxazine (16a)

spironaphthoxazine (17a)

spiroindolinopyridobenzoxazine (18a)

wherein
A and L are independently of each other selected from the group consisting of H, halogen, C2-C12 alkenyl, C2-C12 alkynyl and

wherein R is C1-C6 alkyl, C1-C6 alkoxy, C6-C14 aryl and C7-C15 aralkyl; wherein said alkenyl, alkynyl and

may be substituted by one or more group selected from halogen, hydroxyl, thiol, amino, alkoxy, nitro, azido, sulfo, aryl and heteroaryl;
Y is selected from the group consisting of C1-C25 alkyl, preferably methyl, n-propyl and n-octadecyl, and C7-C15 aralkyl, wherein said alkyl and aralkyl may be substituted by one or more group selected from halogen, preferably fluorine; and
X is C1-C6 alkoxy or L.

In another embodiment, the present invention also relates to a novel class of spiroaromatic compounds consisting of the derivatives of 1',3',3'-trimethyl-6-nitro-spiro(2H-1-benzopyran-2,2'-2H-indole) as given in Formula (IV):

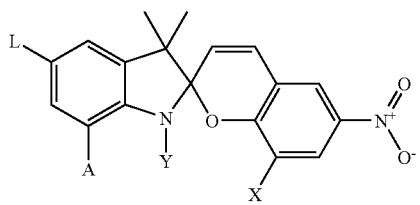
(IV)

wherein
A and L are independently of each other selected from the group consisting of H, halogen, C2-C12 alkenyl, C2-C12 alkynyl and

wherein R is C1-C6 alkyl, C1-C6 alkoxy, C6-C14 aryl and C7-C15 aralkyl; wherein said alkenyl, alkynyl and

may be substituted by one or more group selected from halogen, hydroxyl, thiol, amino, alkoxy, nitro, azido, sulfo, aryl and heteroaryl;
Y is selected from the group consisting of C1-C25 alkyl and C7-C15 aralkyl, wherein said alkyl and aralkyl may be substituted by one or more group selected from halogen, preferably fluorine; and
X is C1-C6 alkoxy or L;
with the proviso that Y is not n-propyl when L, A and X are hydrogen.

More preferred are the derivatives of 1',3',3'-trimethyl-6-nitro-spiro(2H-1-benzopyran-2,2'-2H-indole) as given in Formula (IV) wherein L is H; halogen, preferably Cl, Br or I; $CH_3$—$(CH=CH)_n$—$CH=CH_2$, wherein n is an integer of from 1 to 10; or —C≡C-aryl, preferably —C≡C-phenyl;
Y is C1-C25 alkyl or

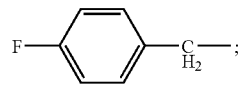

X is hydrogen, methoxy or halogen; and A is hydrogen;
with the proviso that Y is not n-propyl when L, A and X are hydrogen.

It is preferred when L is I, Br or Cl; more preferred when L is I or Br; and most preferred when L is I.

It is also preferred when Y is

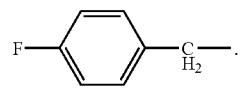

Preferred examples of the derivatives of 1',3',3'-trimethyl-6-nitro-spiro(2H-1-benzopyran-2,2'-2H-indole) as given in Formula (IV) include compounds (19) to (36):

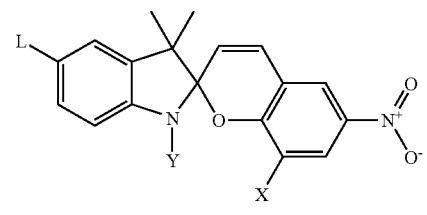
(IV)

| Compound | L | Y | X |
|---|---|---|---|
| 19 | H | methyl | H |
| 21 | H | n-octadecyl | H |
| 22 | H | ![F-phenyl-CH2] | H |
| 23 | Cl | methyl | H |
| 24 | Cl | n-propyl | H |
| 25 | Cl | n-octadecyl | H |
| 26 | Cl | ![F-phenyl-CH2] | H |
| 27 | Br | methyl | H |
| 28 | Br | n-propyl | H |
| 29 | Br | n-octadecyl | H |
| 30 | Br | ![F-phenyl-CH2] | H |
| 31 | I | methyl | H |
| 32 | I | n-propyl | H |
| 33 | I | n-octadecyl | H |

(IV)

[Structure of spiroaromatic compound with substituents L, Y, X]

| Compound | L | Y | X |
|---|---|---|---|
| 34 | I | F—⟨benzene⟩—CH₂— | H |
| 35 | H | F—⟨benzene⟩—CH₂— | methoxy |

The spiroaromatic compounds (22), (32) and (34) are especially preferred.

As used therein, the term "substituted" refers to a radical in which any one or more of the existing C—H bonds is replaced by a C—W bond wherein the W atom may be any one or more of the indicated substituent groups, or a combination thereof. For example, the expression "said . . . aryl . . . may be substituted by one or more group selected from halogen, hydroxyl, thiol, amino, alkoxy, nitro, azido, or sulfo" refers to an aryl group possibly being substituted by the indicated groups, resulting in substituted aryl radicals such as, and not limited to, 4-chlorophenyl, 3-biphenyl, 1-aminopropane-2-ol-phenyl, 2-methylsulfonyl-3-nitromethoxyphenyl and the like.

The term "derivative" as used herein, refers to a compound similar in structure to the another compound, and which may be produced from said another compound in one or more steps as in replacement of H by an alkyl, acyl, amino or any other group. Also contemplated as derivatives are charged systems of their corresponding neutral compounds. For example, within the scope of the present invention, compound 14 is considered as a derivative of compound 12.

The term "endocyclic double bond" refers to cyclic radicals which contain one or more C=C, C=Y and/or Y=Y inner-cycle double bonds wherein C is a carbon atom and Y is a heteroatom such as, but not limiting to, N, O, or S. When Y is a divalent heteroatom such as O or S, the system may be charged. Examples for C=C and C=Y endocyclic double bonds are, without being limited to, cyclopentenyl, cyclohexenyl, benzopyrenyl, indolyl, 2H-benzo[e][1,3]oxazinyl, indazolyl and the like. The term "exocyclic double bond" refers to a cyclic radical which contains one or more C=C, C=Y and/or Y=Y out-of-ring double bond wherein Y is as defined above. Examples for cyclic radicals containing exocyclic double bond are, without limiting thereto, dihydrofuryidione, furyl-2,5-dione, cyclopent-1-yl-3-one, 3,3,4,4-tetrafluoro-5-methylenecyclopenten-1-yl and the like.

The term "alkyl" typically refers to a straight or branched alkyl radical and includes for example methyl, ethyl, n-propyl, isopropyl, n-butyl, isobutyl, tert-butyl, n-pentyl, 2,2-dimethylpropyl, n-hexyl and the like. Preferred alkyl groups are methyl, ethyl and propyl. The term "alkenyl" refers to a straight or branched hydrocarbon radicals typically having between 2 and 6 carbon atoms and one preferably a terminal double bond and includes for example vinyl, prop-2-en-1-yl, but-3-en-1-yl, pent-4-n-1-yl and the like. The terms "alkoxy", "alkylthio" and "alkanoyl" refer to the groups alkyl-O—, alkyl-S—, and alkyl-CO— respectively, wherein "alkyl" is as defined above. Examples of alkoxy are methoxy, ethoxy, hexoxy and the like. Examples of alkylthio are methylthio, propylthio, pentylthio and the like, and examples of alkanoyl are acetyl, propanoyl, butanoyl and the like.

The term "aryl" as used herein refers to aromatic carbocyclic group having 6 to 14 carbon atoms consisting of a single ring or multiple rings such as phenyl, nephthyl, phenanthryl and the like. The term "heteroaryl" refers to monocyclic, bicyclic or tricyclic heteroaromatic group containing one to three heteroatoms selected from N, S and/or O such as, but not limited to, pyridyl, pyrrolyl, furyl, thienyl, imidazolyl, oxazolyl, quinolinyl, thiazolyl, pyrazolyl, quinazolinyl, 1,3,4-triazinyl, 1,2,3-triazinyl, benzofuryl, isobenzofuryl, indolyl, imidazo[1,2-a]pyridyl, benzimidazolyl, benzthiazolyl and benzoxazolyl.

The term "halogen" refers to fluoro, chloro, bromo or iodo. The term "perfluoro" or "perfluorated" refers to a radical in which all hydrogen atoms were replaced by F atoms. For Example, a perfluorated methyl group refers to —CF₃.

Also contemplated by the present invention are TTIs which use charged compounds of Formulae (I), (II) or (III). The negatively charged systems may be formed with metals or amines such as alkali and alkaline earth metals or organic amines. Examples of metals used as cations are sodium, potassium, magnesium, calcium and the like. The cations may also be quaternary salts such as a quaternary salt of the formula —NRR'R"+Z wherein R, R' and R" each is independently hydrogen, alkyl or benzyl and Z is a counterion, including chloride, bromide, iodide, O-alkyl, toluenesulfonate, methylsulfonate, sulfonate, phosphate, benzoate, borate or carboxylate.

Acid addition salts of the compounds include salts derived from inorganic acids such as hydrochloric, nitric, phosphoric, sulfuric, hydrobromic, hydroiodic, phosphorous and the like, as well as salts derived from organic acids such as aliphatic mono- and dicarboxylic acids, phenyl-substituted alkanoic acids, hydroxyl alkanoic acid, aromatic acids, sulfonic acids and the like. Such salts thus include cations such as sulfate bisulfate, bisulfite, nitrate, phosphate, monohydrogenphosphate, metaphosphate, chloride, bromide, iodide, acetate, propionate, isobutyrate, oxalate, malonate and the like.

The acid addition salts forming positively charged compounds, to be used with the TTIs of the present invention, may be prepared by contacting the free base derivatives of the compounds of general Formulas I, II or III with a sufficient amount of the desired acid to produce the salt in the conventional manner. The free base may be re-generated by contacting the salt form with a base and isolating the free base.

The positively charged systems may also be prepared by contacting the free base compounds with sufficient amounts of an alkylating agent such as alkylhalides, e.g., methyliodide, methylbromide and the like to affect substitution at the heteroatom. The negatively charged counterion, being an atom or a group, such as bromide, hydroxide, carbonate and the like may be replaced by a different negatively charged counterion utilizing any method known in the art.

Within the scope of the present invention, the term "charged heteroatom" or "charged heteroaryl" refers to heteroaryl systems, as defined hereinbefore, being singly charged or multiply charged, having a localized charge or a delocalized charge.

Localized charge may reside on one or more atom. In case of a fully substituted heteroatom, such as tetrasubstituted N atom, the charge would be positive, as described hereinbefore. The heteroaryl may also be negatively charged, as described hereinbefore, wherein the heteroatom is partially substituted having an unbonding pair of electrons. In positively and negatively charged systems, carbon atoms may also take on the charge, not necessarily via delocalization of distant charge.

The term "charged group" refers to any one or more groups capable of taking on negative or positive charge or charges. Examples of such groups are ammonium, phosphonium, phenolate, carboxylate, sulphonate, thiolate, selenate and those mentioned herein before. The charge may be localized or delocalized and may be positive or negative. The term "group substituted by another group having a charge" refers to neutral radicals being substituted by charged groups as defined hereinbefore. The terms charged heteroatoms, charged heteroaryl, or charged group encompass zwitterionic systems as well.

The synthesis of the compounds used with the indicators of the present invention, may be prepared according to any synthetic route known in the literature. FIGS. 2, 6 and 7 show examples of such syntheses.

In accordance with another aspect of the present invention, there is provided a means of producing a time temperature indicator having active matrices that contain at least one of the inventive indicator compounds described above, preferably an indicator compound selected from diarylethene and/or spiroaromatic materials.

In a preferred embodiment of the present invention, the indicator compound as the active material of the time-temperature indicator is provided in an ink formulation, which is directly printed onto said packaging material or label.

In yet another aspect of the present invention, there is provided a method for the manufacture of a TTI comprising an active material including at least one of the indicator compound described above, preferably selected from the reversible photochromic indicators described above and more preferably selected from the diarylethenes and/or spiroaromatics described above, said method comprising: embedding in or a top a suitable matrix said at least one indicator compound; and inducing formation of a metastable state of the embedded at least one indicator compound. In one embodiment, the method further comprises covering said TTI with a suitable cover support. Preferably, the cover support is designed to avoid photo recharging or photo bleaching.

Depending on the specific application, a diarylethene or a spiroaromatic compound having the required behavior may be chosen. Most of the above systems and all of the examples are characterized in that a non-colored thermodynamically stable state and a colored metastable state is used. Yet, these molecules are characterized by a relatively high optical quantum yield for the activation process turning the molecules colored and a substantially low optical quantum yield for the time and temperature dependent reaction process turning the molecules discolored. In the colored state, only negligible effect is found to any stimulus other than temperature. When the inventive TTI relies on diarylethenes, the activation process preferably includes a ring closure (or a ring opening step when spiroaromatics are used) and the discoloration process is preferably accompanied with a ring opening (or ring closure in case of spiroaromatic compounds).

The metastable state of the compounds used with the TTIs of the present invention may be achieved by one of the various stimuli mentioned hereinabove. In one embodiment, the metastable state is generated by photonic induction, wherein a matrix embedded with the substance is positioned or passed under a light source, emitting light of a wavelength and intensity suitable for photoexcitation, such as UV. The exposure to the light is terminated when the embedded substance changes its color to a color indicative of the formation of the metastable state at a pre-fixed quantity.

In another embodiment, the metastable state is achieved by pressure induction. In this procedure, the matrix embedded with and/or atop the substance is passed between two bodies, such as metal rolls, which apply pressure onto the surface of the matrix thereby inducing the formation of the metastable state. By adjusting the time and pressure imparted by the bodies to the active material, it is possible to control the degree of conversion from a stable state to a metastable state in the TTI active matrix.

In yet another embodiment, the metastable state is achieved by thermal induction. In this particular induction process, the matrix embedded with the substance to be induced is heated to temperatures normally below the melting point of said substance. The heat may be applied by any method known. In one specific case, the heat is applied to the matrix while being passed trough two heated metal rolls. In this case, the pressure applied to the surface is not capable itself of inducing the formation of the metastable state, but serves merely to ensure controlled thermal contact between the heaters and the sample. The metastable state is achieved as a result of the heat transfer from the heaters, i.e., the metal rolls, which are in contact with the matrix and the matrix itself.

However, there may be instances where the use of any combination of pressure, light and thermal inductions may be desired or necessary. It is therefore, a further embodiment of the present invention, to achieve the metastable state of the substances to be used with the TTIs of the present invention, by a combination of stimuli.

The support matrix used in the present invention may be a polymer such as PVC, PMMA, PEO polypropylene, polyethylene, all kinds of paper, all kinds of printing media or the like or any glass-like film. The active indicator may be introduced into and/or atop a matrix substrate such as polymers, glass, metals, paper, and the like, and may take on in the matrix any form that may permit reversibility of the induced chromic process. Such forms may be or result from indicator-doping of the matrix, sol-gel embodiment of the indicator in the matrix, embodiment of the indicator as small crystallites, solid solution and the like.

In one case, the depositing of the active material in the process of producing the TTI of the present invention is by transforming it into a printable ink that is suitable for printing using any of the printing methods known in the art, e.g., ink jet printing, flexo printing, laser printing and the like.

In another specific embodiment, the active indicator is embedded in the matrix in the form of small crystallites. In yet another specific embodiment, the active indicator is embedded in the packaging material of the goods.

The time temperature indicator according to the present invention is preferably packaged and/or attached to perishable items, especially to pharmaceuticals, biologicals or food items.

In another embodiment, the present invention also relates to a method of time temperature indication comprising the step of converting an indicator in a valence isomerization reaction without migration of an atom or group attached to said indicator in a time and temperature dependent manner, wherein the conversion of a first isomeric form of said indicator into a second isomeric form is detected by monitoring a physical characteristic of the first or second isomeric form of said indicator corresponding to its concentration.

Preferably, the formation of the reaction product is visualized by a change of color based on the color difference between the two isomeric forms of the indicator.

In a specific embodiment, the present invention also relates to a method of determining the quality of ageing- and temperature-sensitive products, which comprises the following steps:
a) printing onto a substrate a time-temperature integrator which comprises at least one indicator having photochromic properties based on a valence isomerization reaction without migration of an atom or group attached to said indicator, preferably an indicator selected from diarylethenes and spiroaromatic compounds as defined above,
b) activating the indicator, preferably by photo-induced coloration
c) optionally applying a protector that prevents renewed photo-induced coloration of the indicator, and
d) determining the degree of time- or temperature-induced decoloration and, taking account of the degree of decoloration, the quality of the product.

When ink-jet printing is used, the procedure is advantageously as follows:

In Step a), a time-temperature integrator comprising at least one indicator having photochromic properties based on a valence isomerization reaction without migration of an atom or group attached to said indicator, preferably an indicator selected from diarylethenes and spiroaromatic compounds as defined above, is applied by means of ink-jet printing to the substrate, especially to the packaging of ageing- and temperature-sensitive products or to labels that are applied to the packaging.

In a preferred embodiment, in Step a) it is possible additionally to apply, by means of ink-jet printing, a reference scale which reproduces the change in the color of the indicator as a function of time, and it is possible to apply, preferably in black ink, further text (or information), such as an expiry date, product identification, weight, contents etc.

Step a) is followed by Step b), activation, especially photo-induced coloration of the reversible indicator. The photo-induced curing of the binder advantageously includes the photo-induced coloration of the indicator.

If desired, following Step b), an irreversible photo-sensitive indicator can be applied as tamper-proofing in the form of a covering over the time-temperature integrator. Suitable irreversible indicators include, for example, pyrrole derivatives, such as 2-phenyl-di(2-pyrrole)methane. Such a material turns irreversibly red when it is exposed to UV light.

Step c) is followed by the application of a protector, especially a color filter, which prevents renewed photo-induced coloration of the reversible indicator. In the case of UV-sensitive indicators, there come into consideration yellow filters, which are permeable only to light having typical wavelengths of more than 430 nm. Advantageously the protective film, that is to say the color filter, can likewise be applied by means of ink-jet printing.

The time-temperature clock can be started at a defined desired timepoint. Decoloration is preferred for consideration according to the invention, but the use of an indicator in which the coloration process forms the basis of the time-temperature clock is also conceivable.

The actual determination of the quality of ageing- or temperature-sensitive products is preceded by the activation of the indicator in Step b). At a later timepoint, the degree of time- or temperature-induced decoloration is then measured and the quality of the product is inferred therefrom. When an evaluation is made with the aid of the human eye, it may be advantageous to arrange e.g. alongside or below the substrate a reference scale which allocates a certain quality grade, a certain timepoint etc. to a certain degree of decoloration. When the quality of the product is determined by evaluating the degree of decoloration or coloration, it is therefore preferred to use a reference scale.

The substrate can simultaneously form the packaging material for the perishable products or it can be applied to the packaging material, for example in the form of a label.

In yet another embodiment, the present invention also relates to a method of printing a packaging material or a label, comprising the step of:
(a) printing onto a substrate a time-temperature integrator which comprises at least one indicator having photochromic properties based on a valence isomerization reaction without migration of an atom or group attached to said indicator, preferably an indicator selected from diarylethenes and spiroaromatic compounds as defined above.

By means of a reference scale printed with the time-temperature integrator, absolute determination of quality grades is possible. The time-temperature integrator and the reference scale are advantageously arranged on a light-colored substrate in order to facilitate reading.

Suitable substrate materials are both inorganic and organic materials, preferably those known from conventional layer and packaging techniques. There may be mentioned by way of example polymers, glass, metals, paper, cardboard etc.

The substrates are suitable for use as packaging materials for the goods and or for attachment thereto by any method known. It should be understood, that the indicators of the present invention may also be applicable to and used in the food industry, and essentially be similarly effective to other goods that may be used in the pharmaceutical or medical fields.

The present invention also relates to a printing ink or printing ink concentrate that comprises an indicator, wherein said indicator is capable to undergo a valence isomerization reaction without migration of an atom or group attached to said indicator in a time and temperature dependent manner characterized by the conversion of a first isomeric form of said indicator into a second isomeric form and wherein said conversion is detected by monitoring a physical characteristic of the first or second isomeric form of said indicator corresponding to its concentration.

Preferably, the printing ink or printing ink concentrate comprises at least one of the spiroaromatic compounds of general Formula (IV) as decribed above.

The inks preferably comprise a total content of indicators of from 1 to 35% by weight, especially from 1 to 30% by weight and preferably from 1 to 20% by weight, based on the total weight of the ink. As lower limit, a limit of 1.5% by weight, especially 2% by weight and more especially 3% by weight, is preferred.

The printing ink is, for example, a liquid or paste-form dispersion comprising colorant (indicator), binder and optionally solvent and/or optionally water and additives. In a liquid printing ink, the binder and, where applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks.

The printing inks can be used, for example, for electrophotography, intaglio printing, flexographic printing, screen printing, offset printing, lithography or letterpress printing. Suitable printing inks are both solvent-based printing inks and water-based printing inks. Of interest are, for example, printing inks based on aqueous acrylates. Such inks are to be understood as including polymers or copolymers that are obtained by polymerisation of at least one monomer containing a group

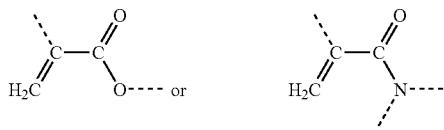

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclohexanone, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations. For intaglio or flexographic printing, a printing ink is usually prepared by dilution of a printing ink concentrate and can then be used in accordance with methods known per se. The printing inks may, for example, also comprise alkyd systems that dry oxidatively. The printing inks are dried in a known manner customary in the art, optionally with heating of the coating. A suitable aqueous printing ink composition comprises, for example, an enzyme-specific substrate, a dispersant and a binder.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids.

The arylsulfonic acid/formaldehyde condensation products are obtainable, for example, by sulfonation of aromatic compounds, such as naphthalene itself or naphthalene-containing mixtures, and subsequent condensation of the resulting arylsulfonic acids with formaldehyde. Such dispersants are known and are described, for example, in U.S. Pat. No. 5,186,846 und DE-A-197 27 767. Suitable oxalkylated phenols are likewise known and are described, for example, in U.S. Pat. No. 4,218,218 und DE-A-197 27 767. Suitable non-ionic dispersants are, for example, alkylene oxide adducts, polymerisation products of vinylpyrrolidone, vinyl acetate or vinyl alcohol and co- or ter-polymers of vinyl pyrrolidone with vinyl acetate and/or vinyl alcohol. It is also possible, for example, to use polymeric acids which act both as dispersants and as binders.

Examples of suitable binder components that may be mentioned include acrylate group-containing, vinyl-group-containing and/or epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP-A-704 469, EP-A-12 339). Furthermore, in order to obtain the desired viscosity, the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary in the printing and coating industries, for example preservatives (such as glutaric dialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally ≦1% by weight, based on the weight of the preparation.

The printing inks may also, for example, comprise solubilisers, e.g. ε-caprolactam. The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 5 to 9, especially from 6.5 to 8.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria.

Such additives are usually used in amounts of from 0.01 to 1% by weight, based on the total weight of the printing ink.

Printing materials that may be mentioned include, for example:
  cellulosic materials, such as paper, paperboard, cardboard, which may also be varnished or have some other coating,
  metallic materials, such as foils, sheets or workpieces of aluminium, iron, copper, silver, gold, zinc or alloys of those metals, which may be varnished or have some other coating,
  silicate materials, such as glass, china and ceramics, which may likewise be coated,
  polymeric materials of all kinds, such as polystyrene, polyamides, polyester, polyethylene, polypropylene, melamine resins, polyacrylates, polyacrylonitrile, polyurethanes, polycarbonates, polyvinyl chloride and corresponding copolymers and block copolymers,
  textile materials, knitted goods, woven goods, non-wovens and made-up goods of polyester, modified polyester, polyester blends, cellulosic materials, such as cotton, cotton blends, jute, flax, hemp and ramie, viscose, wool, silk, polyamide, polyamide blends, polyacrylonitrile, triacetate, acetate, polycarbonate, polypropylene, polyvinyl chloride, polyester microfibres and glass fibre fabrics, foodstuffs and cosmetics.

Especially suitable printing materials are e.g. paper, coated paper, cardboard and plastic or metal foils, such as aluminium foils.

Preference is given to printing processes wherein aqueous printing inks are used. The printing of the printing material is preferably effected by means of continous or dropwise ink-jet printing. Aqueous ink-jet inks are preferred.

The inks may be non-aqueous inks, which consist of a solution of the enzyme of the time temperature indicator in an organic solvent or a mixture of organic solvents. Examples of solvents that can be used for this purpose are alkyl carbitols, alkyl cellosolves, dialkylformamides, dialkylacetamides, alcohols, acetone, methyl ethyl ketone, diethyl ketone, methyl isobutyl ketone, diisopropyl ketone, dibutyl ketone, dioxane, ethyl butyrate, ethyl isovalerate, diethyl malonate, diethyl succinate, butyl acetate, triethyl phosphate, ethyl glycol acetate, toluene, xylene, Tetralin or petroleum ether fractions. Examples of solid waxes as solvents that, as ink vehicles, have to be heated first, are stearic or palmitic acid.

The inks may comprise water-miscible organic solvents, for example $C_1$-$C_4$alcohols, e.g. methanol, ethanol, n-propanol, isopropanol, n-butanol, sec-butanol, tert-butanol or isobutanol; amides, e.g. dimethylformamide or dimethylacetamide; ketones or ketone alcohols, e.g. acetone, diacetone alcohol; ethers, e.g. tetrahydrofuran or dioxane; nitrogen-containing heterocyclic compounds, e.g. N-methyl-2-pyrrolidone or 1,3-dimethyl-2-imidazolidone, polyalkylene glycols, e.g. polyethylene glycol, or polypropylene glycol; $C_2$-$C_6$alkylene glycols and thioglycols, e.g. ethylene glycol, propylene glycol, butylene glycol, triethylene glycol, thiodiglycol, hexylene glycol and diethylene glycol; further polyols, e.g. glycerol or 1,2,6-hexanetriol; and $C_1$-$C_4$alkyl ethers of polyvalent alcohols, e.g. 2-methoxyethanol, 2-(2-methoxyethoxy)ethanol, 2-(2-ethoxyethoxy)ethanol, 2-[2-(2-methoxyethoxy)ethoxy]-ethanol or 2-[2-(2-ethoxyethoxy)ethoxy]ethanol; preferably N-methyl-2-pyrrolidone, diethylene glycol, glycerol or especially 1,2-propylene glycol, usually in an amount of from 2 to 30% by weight, especially from 5 to 30% by weight and preferably from 10 to 25% by weight, based on the total weight of the ink.

The inks may also comprise solubilisers, e.g. ε-caprolactam. The printing inks may, inter alia for the purpose of adjusting the viscosity, comprise thickeners of natural or synthetic origin.

Furthermore, the pigment preparations according to the invention, especially when binder curing is to be effected by means of UV radiation, may comprise a photoinitiator which initiates the polymerisation.

Suitable photoinitiators for free radical photopolymerisations, that is to say the polymerisation of acrylates and, if desired, vinyl compounds, are e.g. benzophenone and benzophenone derivatives, such as 4-phenylbenzophenone and 4-chlorobenzophenone, acetophenone derivatives, such as 1-benzoylcyclohexan-1-ol, 2-hydroxy-2,2-dimethylacetophenone and 2,2-dimethoxy-2-phenylacetophenone, benzoin and benzoin ethers, such as methyl, ethyl and butyl benzoin ethers, benzil ketals, such as benzil dimethyl ketal, 2-methyl-1-[4-(methylthio)phenyl]-2-morpholinopropan-1-one, acylphosphine oxides, such as 2,4,6-trimethylbenzoyl-diphenylphosphine oxide and bisacylphosphine oxides.

Suitable photoinitiators for cationic photopolymerisations, that is to say the polymerisation of vinyl compounds or epoxy-group-containing compounds, are, for example, aryidiazonium salts, such as 4-methoxybenzenediazonium hexafluorophosphate, benzenediazonium tetrafluoroborate and toluenediazonium tetrafluoroarsenate, aryliodonium salts, such as diphenyliodonium hexafluoroarsenate, arylsulfonium salts, such as triphenylsulfonium hexafluorophosphate, benzene- and toluene-sulfonium hexafluorophosphate and bis[4-diphenylsulfonio-phenyl]sulfide-bis-hexafluorophosphate, disulfones, such as diphenyl disulfone and phenyl-4-tolyl disulfone, diazodisulfones, imidotriflates, benzoin tosylates, isoquinolinium salts, such as N-ethoxyisoquinolinium hexafluorophosphate, phenylpyridinium salts, such as N-ethoxy-4-phenylpyridinium hexafluorophosphate, picolinium salts, such as N-ethoxy-2-picolinium hexafluorophosphate, ferrocenium salts, and titanocenes.

When a photoinitiator is present in the ink compositions according to the invention, which is generally necessary for binder curing by UV radiation, the content thereof is generally from 0.1 to 10% by weight, preferably from 0.1 to 8% by weight.

Examples of thickeners that may be mentioned include commercially available alginate thickeners, starch ethers or locust bean flour ethers, especially sodium alginate on its own or in admixture with modified cellulose, for example methyl-, ethyl-, carboxymethyl-, hydroxyethyl-, methylhydroxyethyl-, hydroxypropyl- or hydroxypropylmethyl-cellulose, especially having preferably from 20 to 25% by weight carboxymethylcellulose. Synthetic thickeners that may be mentioned are, for example, those based on poly(meth)acrylic acids or poly(meth)acrylamides.

The inks comprise such thickeners e.g. in an amount of from 0.01 to 2% by weight, especially from 0.01 to 1% by weight and preferably from 0.01 to 0.5% by weight, based on the total weight of the ink.

It is also possible for the inks to comprise buffer substances, for example borax, borate, phosphate, polyphosphate or citrate. Examples include borax, sodium borate, sodium tetraborate, sodium dihydrogen phosphate, disodium hydrogen phosphate, sodium tripolyphosphate, sodium pentapolyphosphate and sodium citrate. They are used especially in amounts of from 0.1 to 3% by weight, preferably from 0.1 to 1% by weight, based on the total weight of the ink, in order to establish a pH value of e.g. from 4 to 9, especially from 5 to 8.5.

As further additives, the inks may comprise surfactants or humectants.

As surfactants there come into consideration the commercially available anionic or non-ionic surfactants. Suitable humectants in the inks according to the invention include, for example, urea or a mixture of sodium lactate (advantageously in the form of a 50 to 60% aqueous solution) and glycerol and/or propylene glycol in amounts of preferably from 0.1 to 30% by weight, especially from 2 to 30% by weight.

Furthermore, the inks may also comprise customary additives, for example preservatives (such as glutaric dialdehyde and/or tetramethylolacetyleneurea), anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. Such agents are usually used in amounts of from 0.01 to 1% by weight, based on the total weight of the ink.

The inks can be prepared in customary manner by mixing together the individual constituents in the desired amount of water.

The inks according to the invention are especially suitable for use in recording systems of the kind in which an ink is expressed from a small opening in the form of droplets which are directed towards a substrate on which an image is formed. Suitable substrates are, for example, paper, textile fibre materials, metal foils or plastics foils. Suitable recording systems are e.g. commercially available ink-jet printers for use in paper or textile printing.

Depending upon the nature of the use, it may be necessary for e.g. the viscosity or other physical properties of the ink, especially those properties which influence the affinity of the ink for the substrate in question, to be adapted accordingly.

In ink-jet printing, individual droplets of ink are sprayed onto a substrate in a controlled manner from a nozzle. For this purpose, predominantly the continuous ink-jet method and the drop-on-demand method are used. In the continuous ink-jet method, the droplets are produced continuously and any droplets not required for the printing are conveyed to a collecting vessel and recycled. In the drop-on-demand method, however, droplets are produced and printed as required; that is to say droplets are produced only when required for the printing. The production of the droplets can be effected, for example, by means of a piezo-inkjet head or by means of thermal energy (bubble jet).

The subsequent curing of the binder, that is to say the fixing of the print, can be effected in customary manner with the aid of heat or high-energy radiation. For this purpose, the print is irradiated either with electrons under an inert gas atmosphere (e.g. nitrogen) (electron beam curing) or with high-energy electromagnetic radiation, preferably in a wavelength range of from 220 to 450 nm. In such a procedure, the chosen light intensities should be matched to the curing speed in order to avoid decomposition of the indicator.

Another embodiment of the present invention concerns a packaging material or a label that comprises a time-temperature indicator as described above.

In yet another embodiment, the present invention also relates to a high molecular weight material that comprises at least one of the spiroaromatic compounds of general Formula (IV) as described above.

The high molecular weight organic material may be of natural or synthetic origin and generally has a molecular weight in the range of from 103 to 103 g/mol. It may be, for example, a natural resin or a drying oil, rubber or casein, or a modified natural material, such as chlorinated rubber, an oil-modified alkyd resin, viscose, a cellulose ether or ester, such as cellulose acetate, cellulose propionate, cellulose acetobutyrate or nitrocellulose, but especially a totally synthetic organic polymer (thermosetting plastics and thermoplastics), as are obtained by polymerisation, polycondensation or polyaddition, for example polyolefins, such as polyethylene, polypropylene or polyisobutylene, substituted polyolefins, such as polymerisation products of vinyl chloride, vinyl acetate, styrene, acrylonitrile, acrylic acid esters and/or methacrylic acid esters or butadiene, and copolymerisation products of the mentioned monomers, especially ABS or EVA. From the group of the polyaddition resins and polycondensation resins there may be mentioned the condensation products of formaldehyde with phenols, so-called phenoplasts, and the condensation products of formaldehyde with urea, thiourea and melamine, so-called aminoplasts, the polyesters used as surface-coating resins, either saturated, such as alkyd resins, or unsaturated, such as maleic resins, also linear polyesters and polyamides or silicones. The mentioned high molecular weight compounds may be present individually or in mixtures, in the form of plastic compositions or melts. They may also be present in the form of their monomers or in the polymerised state in dissolved form as film-forming agents or binders for surface-coatings or printing inks, such as boiled linseed oil, nitrocellulose, alkyd resins, melamine resins, urea-formaldehyde resins or acrylic resins.

In order to better understand the present invention and to see how it may be carried out in practice, preferred embodiments will now be described, by way of non-limiting examples, with reference given to the accompanying drawings, in which:

BRIEF DESCRIPTION OF THE DRAWINGS

FIGS. 1A and 1B schematically illustrate the photosensitivity of the uncharged and charged species of a time temperature monitor based on 2-(2,4-dinitrobenzyl)-3-methylpyridine;

EXAMPLE 1

A Time Temperature Indicator Having a Crystalline Active Matrix Made of the Diarylethene Compound (3)

Crystals of (3) are photochromic in the crystal, forming a deep color upon illumination. In the dark, the cyclic photoproduct reverts to the stable colorless form ($\tau_{1/2}$=37 s at room temperature).

EXAMPLE 2

A Time Temperature Indicator Having a Crystalline Active Matrix Made of N-Propyl Nitrospiropyrane (11)

(a) Synthesis

Figure 2:
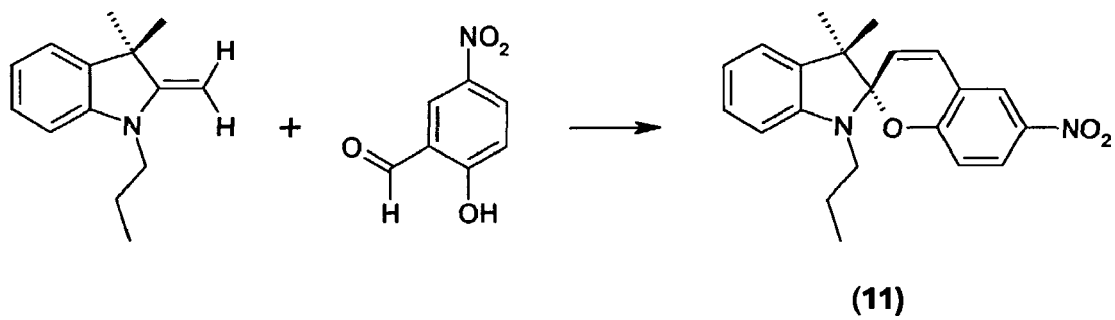
FIG. 2 depicts the synthesis of compound (11).

N-propyl nitrospiropyran (11) was prepared as shown in FIG. 2 by refluxing a mixture of 3,3-dimethyl-2-methylene-1-propyl-2,3-dihydro-1H-indole and 2-hydroxy-5-nitrobenzaldehyde in ethanol. The product was purified by column chromatography and recrystallized from ethanol.

(b) Properties

Figure 3:
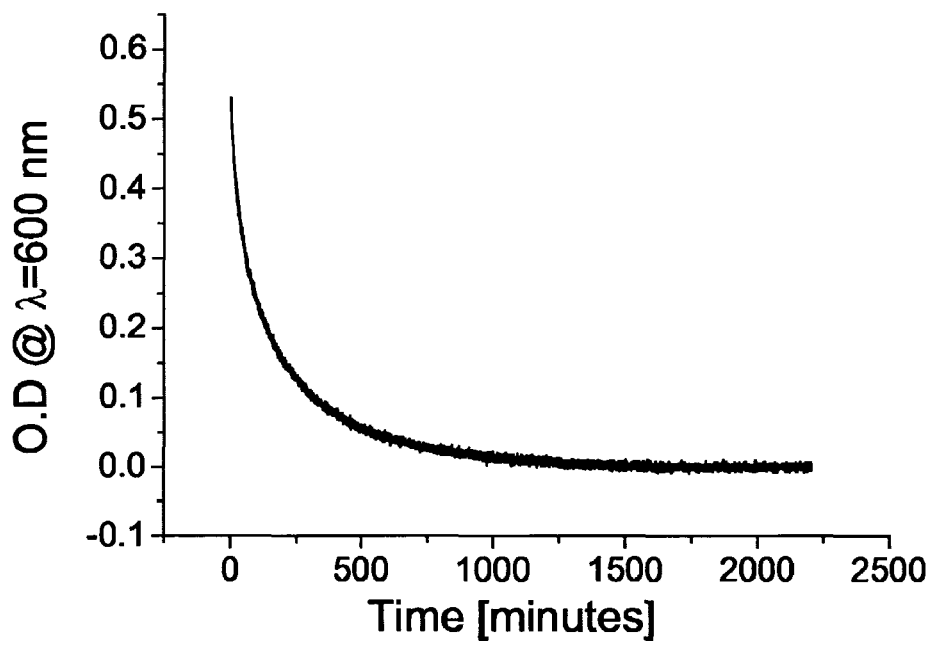
FIG. 3 depicts the reversion of the metastable state of compound (11) to its corresponding colorless state.
Figure 4:
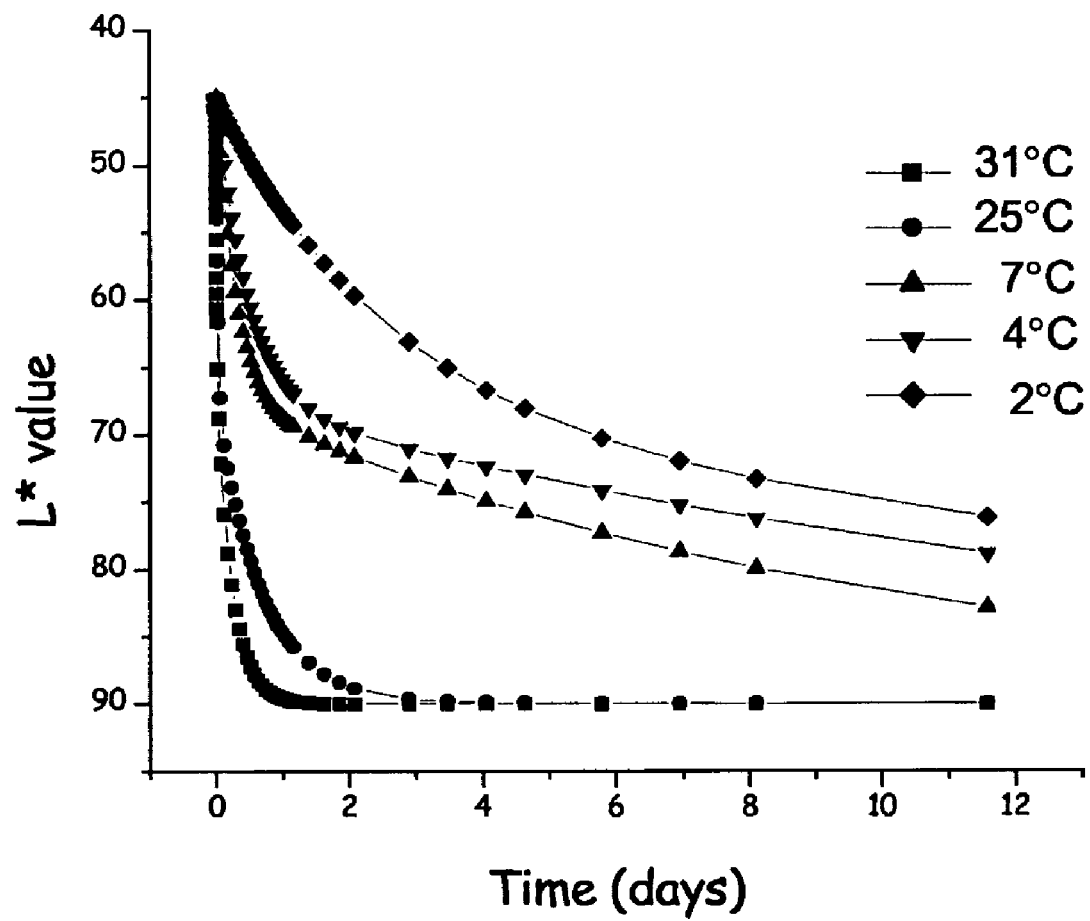
FIG. 4 depicts the reversion of metastable state of compound (11) as a function of temperature.

Compound (11) is photochromic in the crystal, forming a deep blue purple color upon illumination, as shown in FIG. 3. In the dark, the acyclic photoproduct reverts to the stable colorless form following a biexponential decay curve, the fading rate being proportional to the aggregated heat adsorbed by the system and thus serving as an indicator to the time—temperature history it experienced during its colored period (FIG. 4).

(c) Preparation of the TTI

Finely ground powder of colorless (11) was suspended in an inert solvent and adsorbed onto a paper support. Alternatively, a solution of the compound in ethanol or an ether: hexane mixture was sprayed onto the appropriate surface, such as paper, and the solvent evaporated, resulting in crystallization of (11) in the support matrix. The active spot was surrounded by a reference color and encapsulated in between two plastic foils.

In another case, the substrate on which the active matrix is deposited is a transparent polypropylene, which is covered and sealed after deposition of (11) with a polypropylene color filter designed to avoid photo re-charging as well as photo bleaching.

(d) Results

Illumination of the TTI loaded with fine crystalline powder of (11) turned it deep blue. The illumination activates the system as a TTI and in the absence of any additional light illumination the system is sensitive only to the temperature and time. In the dark, the acyclic photoproduct form of the active matrix reverts to the stable colorless form, as shown in FIG. 4. The time-temperature profiles that were recorded on the TTI of the present example are: at 31° C.: having a $\tau_{1/2}$=54 min and 5 hrs
25° C.: having a $\tau_{1/2}$=2.5 hrs and 16.6 hrs
7° C.: having a $\tau_{1/2}$=27.8 hrs and 242.6 hrs
4° C.: having a $\tau_{1/2}$=44 hrs and 397 hrs
2° C.: having a $\tau_{1/2}$=60 hrs and 544 hrs.

Figure 5:
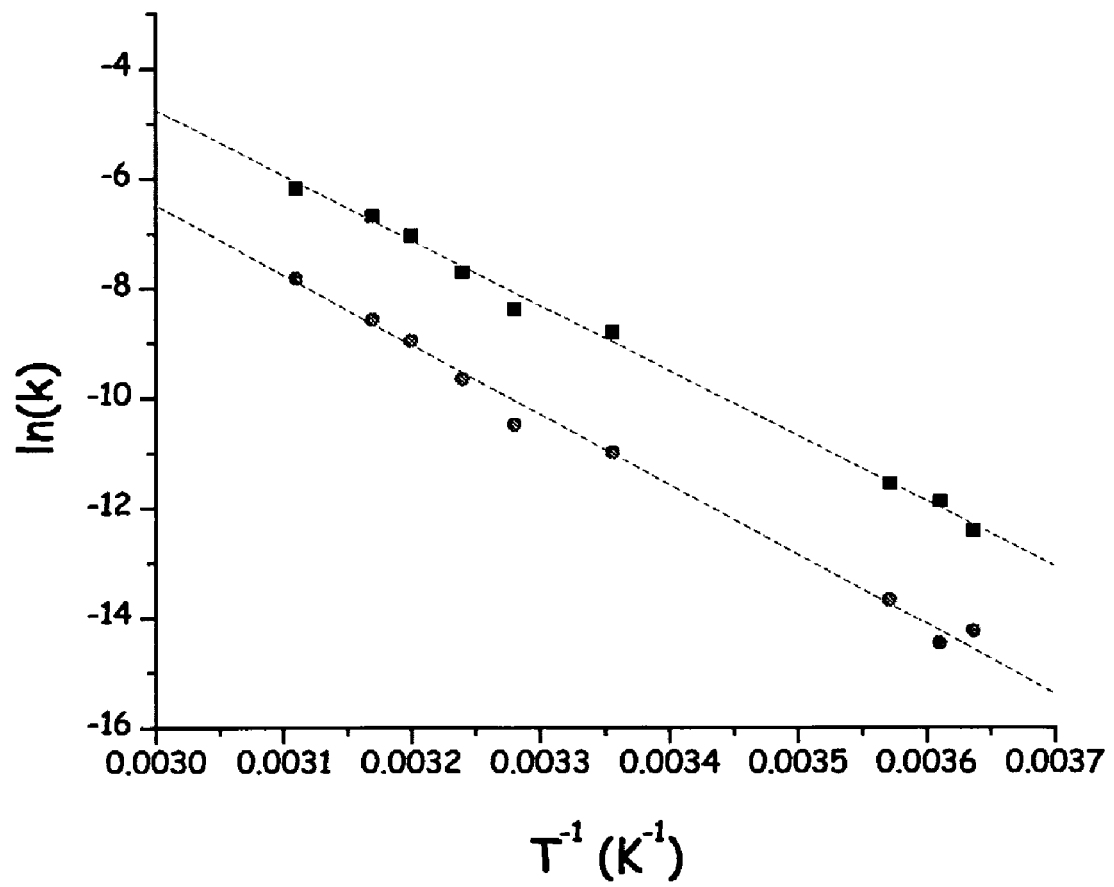
FIG. 5 graphically illustrates the fading rate of compound (11) in terms of its activating energy and preexponential factors.

These results represent activation energies and pre-exponential factors of:
Ea=21.9±0.9 Kcal mol$^{-1}$, A=11.3÷0.8 and
Ea=23.4±0.8 Kcal mol-1, A=13.2±0.6, as shown in FIG. 5.

The fading rate is proportional to the aggregated heat adsorbed by the system and thus is serving as an indicator to the time—temperature history it experienced during its colored period.

EXAMPLE 3

Figure 6:
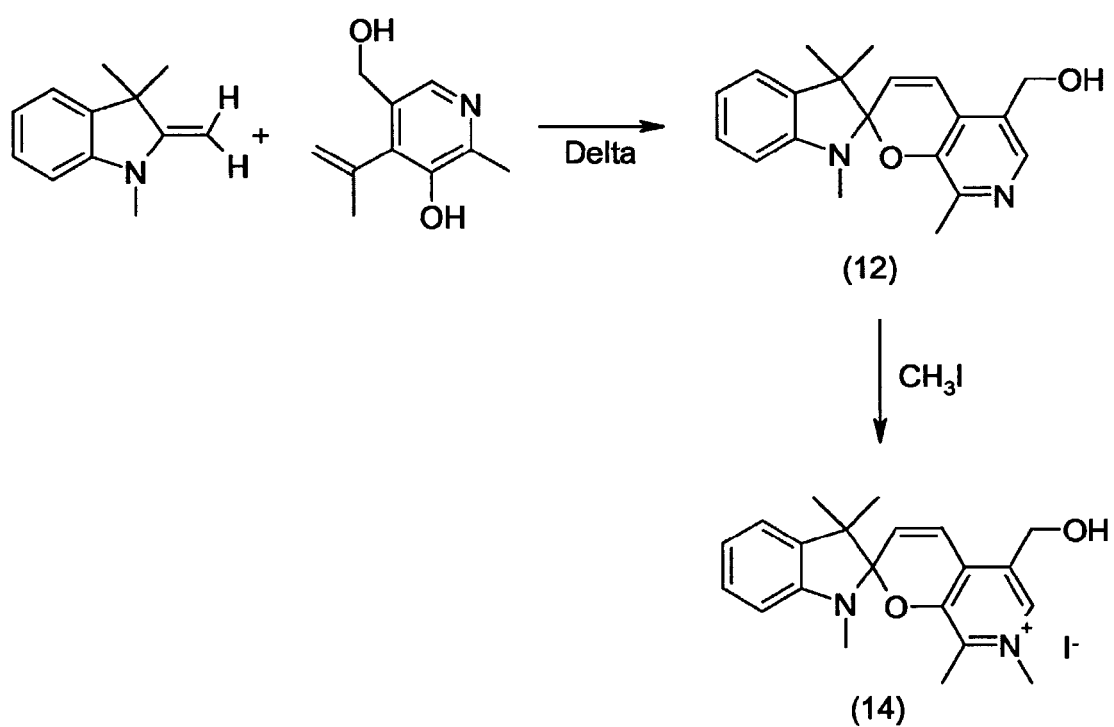
FIG. 6 depicts the synthesis of compounds (12) and (14)
Figure 7:
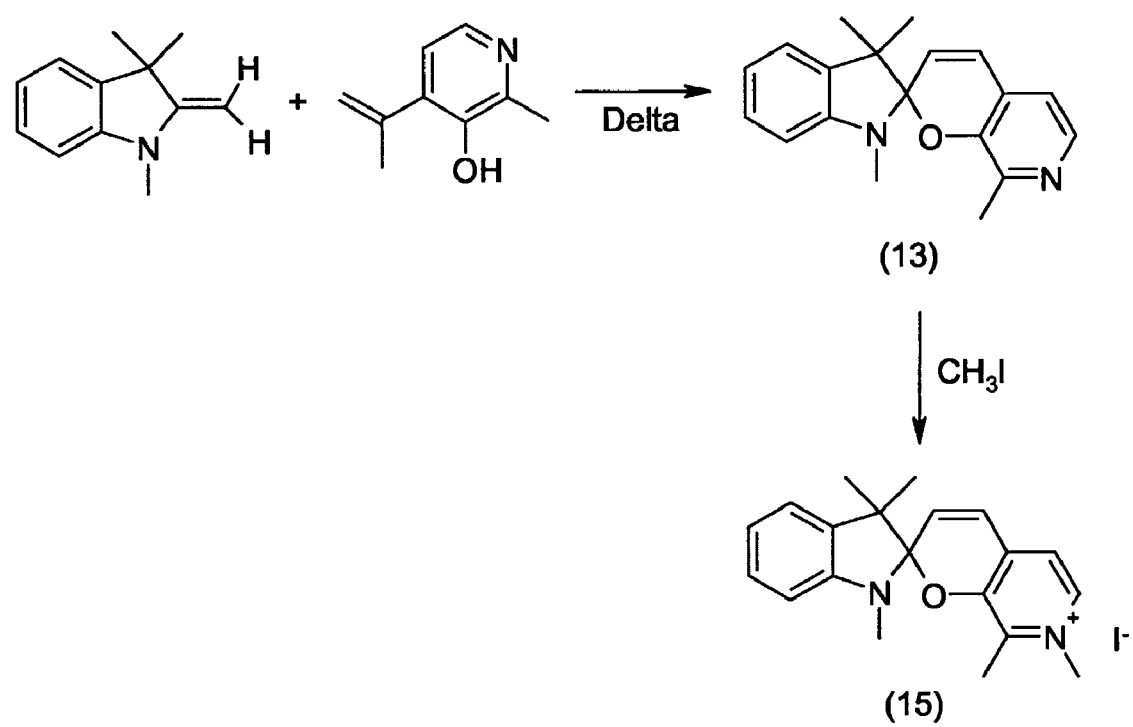
FIG. 7 depicts the synthesis of compounds (13) and (15).

Time Temperature Indicators Having a Crystalline Active Matrix Made of Ionic Spiropyranes (a) Synthesis Ionic spiropyranes (14) and (15) were prepared by refluxing 3,3-dimethyl-2-methylene-1-methyl-2,3-dihydro-1H-indole and the respective salicaldehyde derivative in ethanol, yielding the spiro compounds (12) and (13), shown in FIGS. 6 and 7, respectively. The neutral spiro compounds (12) and (13) were then quarternized, as shown, in the presence of methyl iodide, producing the ionic spiropyranes (14) and (15). The products were easily purified by recrystallization from methanol.

(b) Properties

Compounds (14) and (15) were found to be photochromic in the crystalline state forming a deep red to purple color upon illumination. In the dark, the acyclic photoproducts revert to their stable colorless forms. The fading rate, which is proportional to the aggregated heat adsorbed by the systems and makes these compounds suitable as indicators to the time—temperature history they experienced during their colored period.

In the crystalline state, the photoactivity of (14) and (15), as well as its thermal reversion vary as a function of the specific material but also a function of the specific crystal packing, the later being defined both by the cation but also by the nature and properties of the anion. By changing the anion, either by ion exchange chromatography or by co-precipitation from anti solvent or by any other means known in the art, one can obtain crystalline materials of the same organic substance having different time temperature profiles, thus producing different TTIs having different time-temperature profiles of the same organic substance.

EXAMPLE 4

A Piezochromic Time Temperature Indicator that is Charged by Pressure

Ionic spiropyranes (14) and (15) are piezochromic, turning colored upon applied pressure. Passing a crystalline sample in between two metal drums induces the coloration of the crystals, the spectrum being similar to the photoactivated one. The time-temperature characteristics of the systems were found to be similar to identical systems that were activated by light (results not shown).

The invention claimed is:

1. A time-temperature indicator for indicating a temperature change over time, comprising:
   (a) at least one indicator compound selected from the group consisting of a diarylethene compound and a spiroaromatic compound in a first isomeric form, which is converted into a second isomeric form of said indicator compound in a valence isomerization reaction without migration of an atom or chemical group attached to said indicator compound in a time and temperature dependent manner, wherein the formation of the second isomeric form is detectable by monitoring a physical characteristic of the first isomeric form or the second isomeric form of the indicator, and
   (c) a color filter that substantially filters out only the wavelength ranges causing undesirable renewed coloration of the indicator after the time-temperature clock has started.

2. The time-temperature indicator of claim 1, wherein the diarylethene is a compound of Formula (I)

(I)

wherein:
$R_1$ and $R_2$ each independently represent C6-C14 aryl, C4-C12 heteroaryl, conjugated heterocyclic; wherein said heteroaryl and conjugated heterocyclic may contain one to three heteroatoms selected from the group consisting of N, O, and S; and wherein said aryl, heteroaryl, or conjugated heterocyclic may be substituted by one or more halogen, hydroxyl, thiol, amino, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, cyano, nitro, sulfo, —CH═CH—CN, azido, or amido;
$R_1'$ and $R_2'$ each independently represent H, cyano, nitro, sulfo, hydroxyl, thiol, —CH═CH—CN, or amido; or substituted or unsubstituted C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic; or $R_1'$ and $R_2'$ together with the carbon atoms to which they are attached form a C5-C8 carbocyclic ring or a C4-C7 heterocyclic ring containing one to three endocyclic or exocyclic heteroatoms selected from the group consisting of N, O, and S; said N heteroatom may be further substituted by H, or by one or two substituted or unsubstituted groups selected from the group consisting of C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl, and —CH═CH—CN; when said N heteroatom is tetrasubstituted it is positively charged and is associated with an anion selected from the group consisting of organic and inorganic anions, and optionally wherein said C5-C8 carbocycle is substituted by one or more halogen; and optionally $R_1$, $R_1'$, $R_2$ and $R_2'$ each independently represent a charged group or a group substituted by another group having a charge; said charge may be localized or delocalized and may be positive or negative;

and wherein said $R_1$ and $R_2$ are in a cis or trans conformation.

3. The time-temperature indicator of claim 2, wherein the diarylethene is
(a) a symmetric diarylethene selected from the group consisting of 1,2-dicyano-1,2-bis(2,4,5-trimethylthiophene-3-yl)ethane (1); 2,3-bis(2,4,5-trimethylthiophene-3-yl)maleic anhydride (2); 1,2-bis(2-cyano-1,5-dimethyl-4-pyrrolyl)perfluorocyclopentene (3); and 1,2-bis(2,4-dimethyl-5-phenylthiophene-3-yl)perfluorocyclopentene (4); or
(b) an asymmetric diarylethene selected from the group consisting of 2-(1,2-dimethyl-3-indolyl)-3-(2,4,5-trimethyl-3-thienyl)maleic anhydride (5); and 2-(methoxybenzo[b]thiophene-3-yl)-3-(1,2-dimethyl-3-indolyl)maleic anhydride (6).

4. The time-temperature indicator of claim 1, wherein the spiroaromatic compound is a compound of Formula (II):

wherein:
ring A represents a C5-C8 carbocycle, C4-C7 heterocycle containing at least one heteroatom selected from the group consisting of N, O, and S; said N heteroatom may be further substituted by one or two groups selected from the group consisting of C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl, and —CH═CH—CN; when said N heteroatom is tetrasubstituted it is positively charged and is associated with an anion selected from the group consisting of organic and inorganic anions; said C5-C8 carbocycle or C4-C7 heterocycle may be substituted by one or more of the groups selected from the group consisting of halogen, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, cyano, nitro, sulfo, hydroxyl, thiol, —CH═CH—CN, azido, amido and amino;
ring B represents a substituted or unsubstituted heterocycle containing at least one heteroatom X, said X being selected from the group consisting of N, O, and S; wherein said N atom may be further substituted by one or two groups selected from the group consisting of C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl, and CH═CH—CN; when said N heteroatom is tetrasubstituted it is positively charged and is associated with an anion selected from the group consisting of organic and inorganic anions;

and wherein said ring B may contain one or more endocyclic double bonds and is optionally substituted by one or more halogen;

said rings A and B may be fused to one or more substituted or unsubstituted carbocycle, C4-C14 heterocycle, C6-C14 aryl or C4-C14 heteroaryl ring system;

and wherein the compounds of Formula (II) may be neutral, charged, multiply charged, positively charged having an external anion, negatively charged having an external cation or zwitterionic.

5. The time-temperature indicator of claim 4, wherein the spiroaromatic compound is a spiropyran derivative.

6. The time-temperature indicator of claim 4, wherein the spiropyran derivative is a derivative of 1',3',3'-trimethyl-6-nitro-spiro(2H-1-benzopyran-2,2'-2H-indole) of Formula (III):

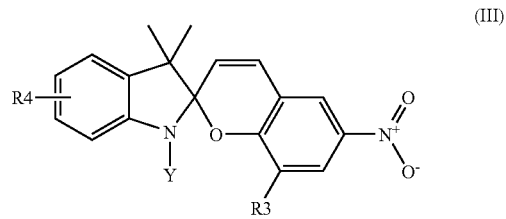

wherein:
R3 is selected from the group consisting of H, halogen, C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, and azido; wherein said alkyl, alkenyl, alkynyl, aryl, heteroaryl, and non-aromatic carbocycle may be substituted by one or more group selected from the group consisting of halogen, hydroxyl, thiol, amino, alkoxy, nitro, azido, and sulfo;

R4 is selected from the group consisting of C1-C12 alkyl, C2-C12 alkenyl, C2-C12 alkynyl, C1-C6 alkanoyl, C1-C6 alkoxy, C1-C6 alkylthio, C6-C14 aryl, C4-C14 heteroaryl, C3-C8 membered non-aromatic carbocyclic, C3-C8 membered ring non-aromatic heterocyclic, hydroxyl and —CH═CH—CN; and Y is selected from the group consisting of C1-C25 alkyl and C7-C15 aralkyl, wherein said alkyl and aralkyl is optionally substituted by one or more halogen.

7. The time-temperature indicator of claim 4, wherein the spiroaromatic compounds include at least one of the following: spirooxazine or its derivatives, spironaphthoxazine or its derivatives, and spiroindolinopyridobenzoxazine or its derivatives.

8. The time-temperature indicator of claim 1, wherein the spiroaromatic compound is a compound of Formula (IV):

(IV)

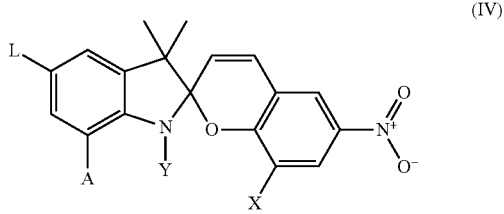

wherein:

A and L are independently of each other selected from the group consisting of H, halogen, C2-C12 alkenyl, C2-C12 alkynyl and

wherein R is C1-C6 alkyl, C1-C6 alkoxy, C6-C14 aryl and C7-C15 aralkyl; wherein said alkenyl, alkynyl and

may be substituted by one or more groups selected from the group consisting of halogen, hydroxyl, thiol, amino, alkoxy, nitro, azido, sulfo, aryl and heteroaryl;

Y is selected from the group consisting of C1-C25 alkyl and C7-C15 aralkyl, wherein said alkyl and aralkyl is optionally substituted by one or more halogen; and X is C1-C6 alkoxy or L;

with the proviso that Y is not n-propyl when L, A and X are hydrogen.

9. The time-temperature indicator of claim 8, wherein

L is hydrogen, Cl, Br or I;

Y is methyl, n-propyl, n-octadecyl or

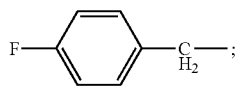

X is hydrogen or methoxy; and

A is hydrogen;

with the proviso that Y is not n-propyl when L and X are hydrogen.

10. A printing ink or printing ink concentrate, comprising the time-temperature indicator of claim 8.

11. A high molecular weight material, comprising the time-temperature indicator of claim 8.

12. A method of manufacturing the time-temperature indicator of claim 1, comprising the steps of
(a) embedding in or atop a matrix at least one indicator compound selected from the group consisting of a diarylethene compound and a spiroaromatic compound;
(b) inducing the formation of a metastable state of said embedded indicator compound; and
(c) covering the time-temperature indicator with a color filter that substantially filters out only the wavelength ranges causing undesirable renewed coloration of the indicator after the time-temperature clock has started.

13. The time-temperature indicator of claim 5, wherein the spiropyran derivative is selected from the group consisting of 1',3',3',8-tetramethyl-5-hydroxymethyl-spiro(2H-pyrano[2,3-c]pyridine-2,2'-2H-indole) and 1',3',3',8-tetramethyl-spiro(2H-pyrano[2,3-c]pyridine-2,2'-2H-indole).

14. The time-temperature indicator of claim 6, wherein in Formula (III) Y is selected from the group consisting of C1-C25 alkyl and C7-C15 aralkyl, wherein said alkyl and aralkyl are substituted by one or more fluorine.

15. The time-temperature indicator of claim 8, wherein in Formula (IV) Y is selected from the group consisting of C1-C25 alkyl and C7-C15 aralkyl, wherein said alkyl and aralkyl are substituted by one or more fluorine.

16. A printing ink or printing ink concentrate, comprising the time-temperature indicator of claim 9.

17. A high molecular weight material, comprising the time-temperature indicator of claim 9.

18. The time-temperature indicator of claim 1, wherein the spiroaromatic compound has the formula

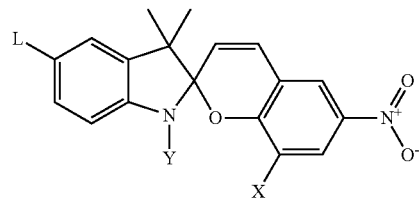

wherein L is hydrogen, Y is

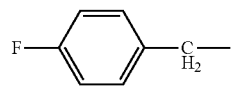

and X is methoxy.

19. A packaging material or a label that comprises a time-temperature indicator for indicating a temperature change over time, comprising:
(a) at least one indicator compound selected from the group consisting of a diarylethene compound and a spiroaromatic compound in a first isomeric form, which is converted into a second isomeric form of said indicator compound in a valence isomerization reaction without migration of an atom or chemical group attached to said indicator compound in a time and temperature dependent manner, wherein the formation of the second isomeric form is detectable by monitoring a physical characteristic of the first isomeric or the second isomeric form of the indicator
(c) a color filter that substantially filters out only the wavelength ranges causing undesirable renewed coloration of the indicator after the time-temperature clock has started, and
(b) a reference scale or reference color for evaluating the degree of decoloration or coloration.

20. The time-temperature indicator of claim 2, wherein $R_1'$ and $R_2'$ together with the carbon atoms to which they are attached form a C5-C8 carbocyclic ring, wherein the C5-C8 carbocyclic ring is substituted by one or more fluorine atoms.

21. The time-temperature indicator of claim 1, further comprising a reference scale for evaluating the degree of decoloration or coloration.

22. The time-temperature indicator of claim 21, wherein the reference scale is a reference color.

23. The time-temperature indicator of claim 1, wherein the at least one indicator compound is present in a crystalline form.

* * * * *